United States Patent [19]
Yamamoto et al.

[11] Patent Number: 6,004,975
[45] Date of Patent: Dec. 21, 1999

[54] BICYCLOLACTAM COMPOUNDS, USE THEREOF AND INTERMEDIATES FOR PREPARING THEREOF

[75] Inventors: Junji Yamamoto, Tokushima; Takashi Arima, Sapporo; Nobuo Kasahara; Masato Nanri, both of Tokushima; Kazuo Ogawa, Tokorozawa; Ichiro Yamawaki, Kawagoe; Manabu Kaneda, Tokorozawa, all of Japan

[73] Assignee: Taiho Pharmaceutical Company Limited, Tokyo, Japan

[21] Appl. No.: 08/908,601

[22] Filed: Aug. 8, 1997

Related U.S. Application Data

[63] Continuation-in-part of application No. 08/537,854, Nov. 15, 1995, abandoned, and a continuation-in-part of application No. 08/776,654, Feb. 7, 1997, abandoned.

[30] Foreign Application Priority Data

| Mar. 28, 1994 | [JP] | Japan | 6-83934 |
| Jun. 12, 1995 | [JP] | Japan | 7-170329 |
| Sep. 27, 1995 | [JP] | Japan | 7-274654 |

[51] Int. Cl.⁶ ................ C07D 221/04; A61K 31/435
[52] U.S. Cl. ........................... 514/299; 546/112
[58] Field of Search .................... 514/299, 309, 514/312; 546/141, 156, 157, 112

[56] References Cited

U.S. PATENT DOCUMENTS

| 5,158,344 | 10/1992 | Kawaguchi et al. | 514/299 |
| 5,214,039 | 5/1993 | Kawaguchi et al. | 514/213 |

FOREIGN PATENT DOCUMENTS

| WO 95/21823 | 8/1995 | WIPO |
| WO 95/21824 | 8/1995 | WIPO |
| WO 95/26187 | 10/1995 | WIPO |

OTHER PUBLICATIONS

Advance Organic Chemistry, Third Editio by Jerry March, pp. 334–335, 1985.

*Primary Examiner*—John M. Ford
*Attorney, Agent, or Firm*—Nikaido Marmelstein Murray & Oram, LLP.

[57] ABSTRACT

A bicyclolactam compound of the formula (1) is disclosed, which has an excellent anxiolytic effect, is high in safety, and is useful as an effective component of medicinals which are greatly diminished in side effects such as hypnotic, muscle relaxant and sedative effects

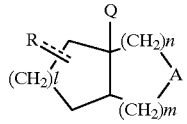

(1)

A bicyclolactam derivative represented by the following formula (1) is also disclosed, and is useful as an effective component of an anxiolytic agent

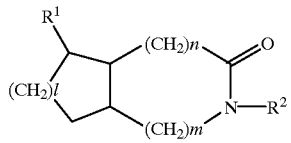

(1)

11 Claims, No Drawings

BICYCLOLACTAM COMPOUNDS, USE THEREOF AND INTERMEDIATES FOR PREPARING THEREOF

This application is a continuation-in-part of U.S. Ser. No. 08/537,854 filed Nov. 15, 1995, now abandoned, and a continuation in part of U.S. Ser. No. 08/776,654 filed Feb. 7, 1997, now abandoned.

TECHNICAL FIELD

The present invention relates to anxiolytic agents comprising a bicyclolactam derivative as their effective component and to the treatment of anxiety.

BACKGROUND ART

With rapid diversification of the social environment in recent years, an increasing number of people are suffering from anxiety, and it has been expected to develop psychosomatic therapies and excellent therapeutic agents.

Benzodiazepine compounds such as diazepam have found wide use as anxiolytics. This group of agents, however, generally have side effects such as hypnotic effect, muscle relaxant effect and sedative effect. Serotonin anxiolytic agents such as buspirone are also recently developed as anxiolytics which are different from the benzodiazepine compounds in activity mechanism. Reportedly these serotonin agents are generally lesser than the benzodiazepines in side effects such as hypnotic, muscle relaxant and sedative effects, but they are lower in anxiolytic effect and have the problems of diminishing voluntary movements presumably owing to their activity as a dopamine antagonist, and causing serotonin syndrome which appears attributable to their properties as a full agonist for serotonin 1A receptor.

On the other hand, the bicyclolactam derivatives of the present invention fire known compounds disclosed in International Public Disclosure No. WO 91/11434, and are known to have a cerebral function improving effect, cerebral metabolism activating or anoxic brain damage protecting effect and effect against senile dementia. Nevertheless, nothing whatsoever is known about the anxiolytic effect of these compounds.

Anxiety is ain essential symptom of neuroses and is a neurotic disorder involving no organic disorder of the brain.

In contrast, the term dementia refers to an organic mental disorder which is the sustained deterioration of acquired intelligence due to an organic disorder of the brain. Many of dementias are caused by a wide variety of organic disorders of the brain and involve general deterioration of mental functions such as memory, calculation, orientation and discretion, leading to failure of correct recognition, judgment or behavior as to one's own situation.

"Diagnostic and Statistical Manual of Mental Disorders," Revised 3rd Ed. (DSM-III-R), widely used as a diagnostic manual and published by American Psychiatric Association in 1987, clearly classifies these diseases in the chapters "Anxiety Disorders (or Anxiety and Phobic Neuroses)" and "Organic Mental Syndromes and Organic Mental Disorders" (see "DSM-III-R Classification of Mental Disorders and Diagnostic Manual," (2nd Ed.), translated by Saburo Takahasi et al., published by Igaku Shoin (1988), pp. 71~94 and 121~129)

An object of the present invention is to provide a novel anxiolytic agent comprising a bicyclolactam derivative as its effective component, and a therapy of anxiety.

DISCLOSURE OF THE INVENTION

We have investigated the pharmacological activities of bicyclolactam derivatives from various viewpoints, consequently found that these compounds have a very high anxiolytic effect and are yet greatly diminished in side effects such as hypnotic, muscle relaxant and sedative effects and accomplished the present invention. More specifically, the invention provides an anxiolytic agent comprising as its effective component a bicyclolactam derivative represented by the following formula

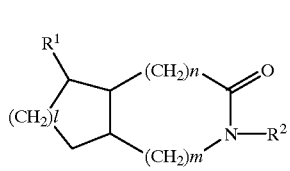

(1)

wherein $R^1$ is a hydrogen atom or hydroxyl group, $R^2$ is benzoyl group which may optionally have at least one substituent, l is 1 or 2, m is 0 or 1 and n is 0, 1 or 2, provided the case where both of m and n represent 0 simultaneously is excluded.

The present invention further includes a method of treating anxiety comprising administering an effective amount of the compound (1) to mammals including man, and also use of the compound (1) for the preparation of medicinals for treating anxiety.

Existing as bicyclolactam derivatives of the formula (1) are stereoisomers due to the presence of the bicyclo ring, and also geometric isomers and optical isomers due to the presence of the carbon atom at the bridgehead position of the bicyclo ring and the carbon atom having $R^1$ attached thereto. The present invention includes all of these isomers.

In view of the numbers l, m and n, the following ten kinds of bicyclo ring skeletons can be present in the compounds of the formula (1). The invention includes all of these cases.

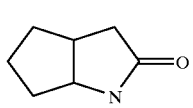

(a)

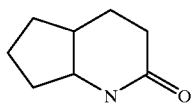

(b)

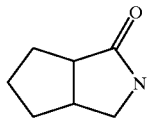

(c)

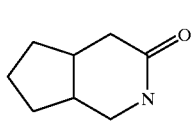

(d)

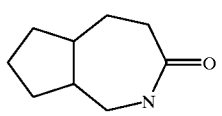

(e)

(f) 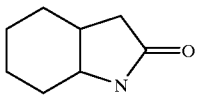

(g) 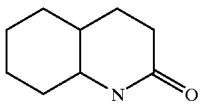

(h) 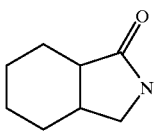

(i) 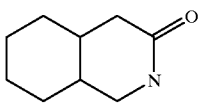

(j) 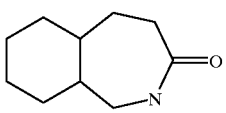

Preferable among these is the case wherein the skeleton is (a), (b), (f), (g) or (h). More preferable is the case wherein m is 0, i.e., (a), (b), (f) or (g). The most preferable is (b), (f) or (g).

According to the invention, examples of substituents which may be present in the benzoyl group represented by $R^2$ are a halogen atom, lower alkyl group, lower alkoxyl group, nitro group, cyano group, hydroxyl group or amino group. Examples of halogen atoms are fluorine, chlorine, bromine and iodine atom, among which chlorine atom is preferable. Examples of useful lower alkyl groups are straight-chain or branched alkyl groups having 1 to 6 carbon atoms, such as methyl, ethyl, n-propyl, isopropyl, n-butyl, isobutyl, tert-butyl, pentyl, isopentyl and hexyl group. Preferable among these are methyl and ethyl groups. Methyl group is more preferable. Examples of useful lower alkoxyl groups are straight-chain or branched alkoxyl groups having 1 to 6 carbon atoms, such as methoxy, ethoxy, n-propoxy, isopropoxy, n-butoxy, isobutoxy, sec-butoxy, tert-butoxy, pentyloxy, isopentyloxy and hexyloxy group, among which methoxy and ethoxy groups are preferable. Methoxy group is more preferable.

Preferable as $R^2$ of the compound represented by the formula (1) is a benzoyl group having as a substituent a halogen atom, lower alkyl group, lower alkoxyl group, nitro group, cyano group or amino group, more preferably a benzoyl group having lower alkoxyl (group. Especially preferable is a benzoyl group having methoxy group. The number of substituents is preferably 1 to 3. The substituent may be present at any of the ortho-, meta- and para-positions on the phenyl ring of the benzoyl group.

Among the compounds of the formula (1), preferable are those wherein m is 0, and more preferable are those wherein $R^2$ is a benzoyl having lower alkoxyl group and wherein l is 1, m is 0 and n is 2, or l is 2, m is 0 and n is 1, or l is 2, m is 0 and n is 2. More preferable are those wherein $R^2$ is a benzoyl group having methoxy group and wherein l is 1, m is 0 and n is 2, or l is 2, m is 0 and n is 1, or l is 2, m is 0 and n is 2. In the case where $R^1$ is hydroxyl group, especially preferred compounds are those wherein l is 1, m is 0 and n is 2.

Examples of the compound of the above formula (1) are
2-(4-methoxybenzoyl)-2-azabicyclo[3.3.0]octane-3-one,
2-(4-methoxybenzoyl)-2-azabicyclo[4.3.0]nonane-3-one,
2-(p-toluyl)-2-azabicyclo[4.3.0]nonane-3-one,
2-(3,4-dichlorobenzoyl)-2-azabicyclo[4.3.0]nonane-3-one,
2-(3,5-dimethoxybenzoyl)-2-azabicyclo[4.3.0]nonane-3-one,
2-(4-cyanobenzoyl)-2-azabicyclo[4.3.0]nonane-3-one,
2-(4-nitrobenzoyl)-2-azabicyclo[4.3.0]nonane-3-one,
2-(4-aminobenzoyl)-2-azabicyclo[4.3.0]nonane-3-one,
2-(4-chlorobenzoyl)-2-azabicyclo[4.3.0]nonane-3-one,
8-(4-methoxybenzoyl)-8-azabicyclo[4.3.0]nonane-7-one,
2-(4-hydroxybenzoyl)-2-azabicyclo[4.3.0]nonane-3-one,
3-(4-methoxybenzoyl)-3-azabicyclo[3.3.0]octane-4-one,
3-(4-methoxybenzoyl)-3-azabicyclo[4.3.0]nonane-4-one,
3-(4-methoxybenzoyl)-3-azabicyclo[5.3.0]decane-4-one,
3-(4-methoxybenzoyl)-3-azabicyclo[4.4.0]decane-4-one,
3-(4-methoxybenzoyl)-3-azabicyclo[5.4.0]undecane-4-one,
7-(4-methoxybenzoyl)-7-azabicyclo[4.3.0]nonane-8-one,
7-(p-toluyl)-7-azabicyclo[4.3.0]nonane-8-one,
7-(3,4-dichlorobenzoyl)-7-azabicyclo[4.3.0]nonane-8-one,
7-(3,5-dimethoxybenzoyl)-7-azabicyclo[4.3.0]nonane-8-one,
7-(4-cyanobenzoyl)-7-azabicyclo[4.3.0]nonane-8-one,
7-(4-nitrobenzoyl)-7-azabicyclo[4.3.0]nonane-8-one,
7-(4-aminobenzoyl)-7-azabicyclo[4.3.0]nonane-8-one,
7-(4-chlorobenzoyl)-7-azabicyclo[4.3.0]nonane-8-one,
7-(4-hydroxybenzoyl)-7-azabicyclo[4.3.0]nonane-8-one,
2-(4-methoxybenzoyl)-2-azabicyclo[4.4.0]decane-3-one,
2-(p-toluyl)-2-azabicyclo[4.4.0]decane-3-one,
2-(3,4-dichlorobenzoyl)—2-azabicyclo[4.4.0]decane-3-one,
2-(3,5-dimethoxybenzoyl)-2-azabicyclo[4.4.0]decane-3-one,
2-(4-cyanobenzoyl)-2-azabicyclo[4.4.0]decane-3-one,
2-(4-nitrobenzoyl)-2-azabicyclo[4.4.0]decane-3-one,
2-(4-aminobenzoyl)-2-azabicyclo[4.4.0]decane-3-one,
2-(4-chlorobenzoyl)-2-azabicyclo[4.4.0]decane-3-one,
2-(4-hydroxybenzoyl)-2-azabicyclo[4.4.0]decane-3-one,
7-hydroxy-2-(4-methoxybenzoyl)-2-azabicyclo[4.3.0]nonane-3-one,
2-hydroxy-7-(4-methoxybenzoyl)-7-azabicyclo[4.3.0]nonane-8-one and
7-hydroxy-2-(4-methoxybenzoyl)-2-azabicyclo[4.4.0]decane-3-one.

Preferable examples are
2-(4-methoxybenzoyl)-2-azabicyclo[4.4.0]decane-3-one,
2-(4-methoxybenzoyl)-2-azabicyclo[3.3.0]octane-3-one,
2-(4-methoxybenzoyl)-2-azabicyclo[4.3.0]nonane-3-one,
2-(p-toluyl)-2-azabicyclo[4.3.0]nonane-3-one,
2-(3,4-dichlorobenzoyl)-2-azabicyclo[4.3.0]nonane-3-one,
2-(3,5-dimethoxybenzoyl)-2-azabicyclo[4.3.0]nonane-3-one,
2-(4-cianobenzoyl)-2-azabicyclo[4.3.0]nonane-3-one,
2-(4-nitrobenzoyl)-2-azabicyclo[4.3.0]nonane-3-one,
2-(4-aminobenzoyl)-2-azabicyclo[4.3.0]nonane-3-one,
2-(4-chlorobenzoyl)-2-azabicyclo[4.3.0]nonane-3-one,
7-(4-methoxybenzoyl)-7-azabicyclo[4.3.0]nonane-8-one,
8-(4-methoxybenzoyl)-8-azabicyclo[4.3.0]nonane-7-one and
7-hydroxy-2-(4-methoxybenzoyl)-2-azabicyclo[4.3.0]nonane-3-one, More preferable examples are
2-(4-methoxybenzoyl)-2-azabicyclo[4.4.0]decane-3-one,
2-(4-methoxybenzoyl)-2-azabicyclo[4.3.0]nonane-3-one, 7-(4-methoxybenzoyl)-7-azabicyclo[4.3.0]nonane-8-one and 7-hydroxy-2-(4-methoxybenzoyl)-2-azabicyclo[4.3.0] nonane-3-one.

The bicyclolactam derivative of the formula (1) is a known compound which is disclosed for example in International Public Disclosure No. WO 91/11434 (U.S. Pat. No. 5,185,344, U.S. Pat. No. 5,214,039), etc.

The bicyclolactam derivative (1-a) of the present invention wherein $R^1$ is hydrogen atom can be prepared, for example, by the following reaction process

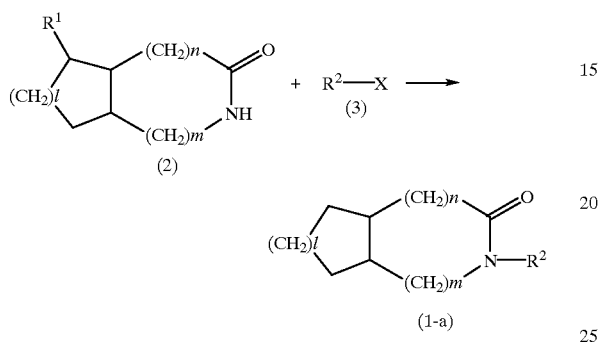

wherein $R^2$, l, m and n are as defined above, X is halogen atom.

Bicyclolactam compound (2) is a known compound and is easily prepared by methods disclosed in Journal of American Chemical Society, 77, 409 (1955), Yakugaku Zasshi, 84, 674 (1964) and Journal of Chemical Society Perkin Transactions I 11, 2563 (1982). The compound of the formula (1-a) can be prepared by reacting the bicyclolactam compound (2) with the halide compound (3), in the presence of a base in an appropriate solvent.

The solvent is not limited specifically insofar as it does not participate in the reaction. Examples of solvents generally useful are hydrocarbon halides such as dichlorolmethane and chloroform, ethers such as ethyl ether and tetrahydrofuran, aromatic hydrocarbons such as benzene and toluene, aprotic polar solvents such as N,N-dimethylformamide and dimethylsulfoxide.

As to the proportion of the compound (2) and the halide compound (3), it is usual to use 0.5 to 2 moles, preferably one mole of the compound (3) per mole of the compound (2). Examples of bases are organic amines such as triethylamine, pyridine and 4-dimethylaminopyridine, and inorganic bases such as sodium hydride and sodium amide. The amount of the base is usually 0.5 to 2 moles, preferably one mole per mole of the compound (2). The reaction temperature is 0 to 150° C., preferably 50 to 100° C. The reaction time is 1 to 48 hours, preferably 2 to 12 hours.

The bicyclolactam derivative (1-b) of the present invention wherein $R^1$ is hydroxyl group can be prepared, for example, by the following reaction process

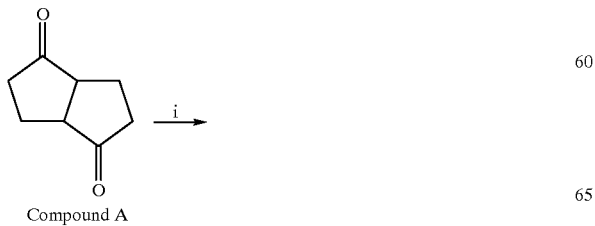

Compound A

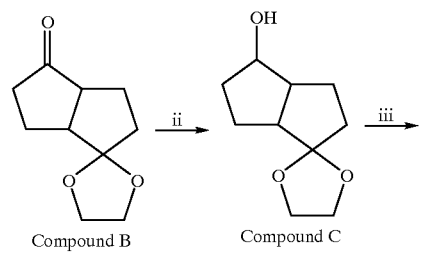

Compound B      Compound C

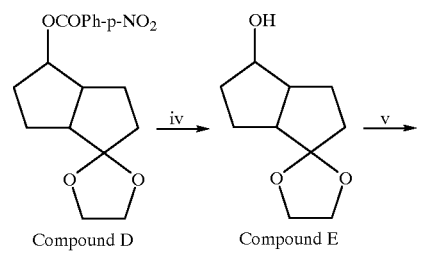

Compound D      Compound E

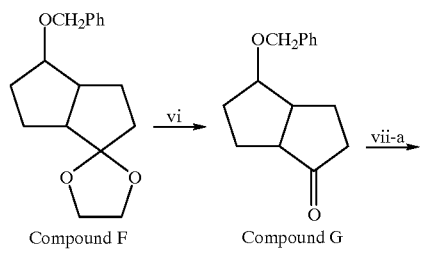

Compound F      Compound G

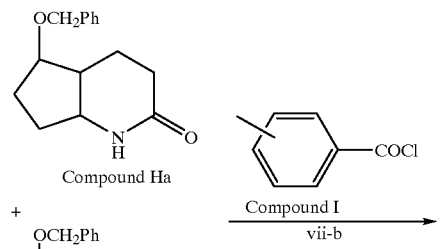

Compound Ha

+

Compound Hb

Compound I

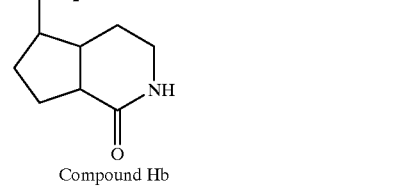

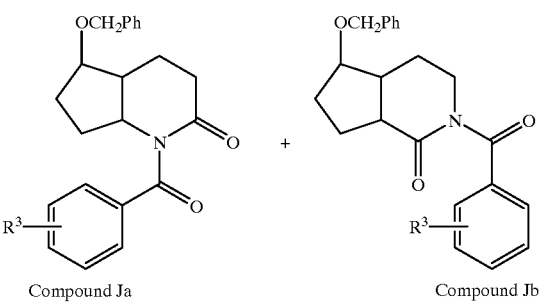

Compound Ja      Compound Jb

↓ viii

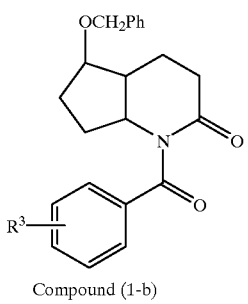

Compound (1-b)

wherein R³ is hydrogen atom, halogen atom, lower alkyl group, lower alkoxyl group, nitro group, cyano group, hydroxyl group or amino group.

(i) A known compound A disclosed in J. Org. Chem., 42, 3764–3767(1977) is reacted with ethylene glycol in a suitable solvent in the presence of an acid catalyst to obtain a compound B. The solvent to be used is not particularly limited insofar as it does not participate in the reaction; it is, for example, an aromatic hydrocarbon such as benzene, toluene or xylene. Examples of useful acid catalysts are sulfuric acid, p-toluenesulfonic acid, methanesulfonic acid, trifluoromethanesulfonic acid the like. The reaction is conducted using ethylene glycol and the acid catalyst each in an amount of about 1 to about 2 moles per mole of the compound A. The reaction temperature is 80° C. to a temperature around the boiling point of the solvent. For the completion of the reaction, the reaction time is 1 to 8 hours, preferable about 4 to about 7 hours. The compound B obtained by the reaction can be used for the subsequent reaction, as isolated or without being isolated.

(ii) Next, the compound B is reacted with a reducing agent in a suitable solvent to obtain a compound C. The solvent to be used is not limited specifically insofar as it does not participate in the reaction. Examples of such solvents are methanol, ethanol, propanol, isopropanol and like alcohols, dioxane, 1,2-dimethoxyethane, tetrahydrofuran and like ethers. Examples of useful reducing agents are lithium aluminum hydride, diisobutyl aluminum hydride, diborane, sodium boron hydride and the like. The reaction is conducted using the reducing agent in about 1 to about 1.5 moles per mole of the compound C. The reaction temperature is −5° C. to room temperature, preferably about 0 to about 10° C. The reaction time is preferably about 1 to about 3 hours. The compound C resulting from the reaction can be used for the subsequent reaction, as isolated or without being isolated.

(iii) The compound C is reacted with p-nitrobenzoic acid, triphenylphosphine and diethyl azodicarboxylate in a suitable solvent to obtain a compound D. The solvent to be used is not limited specifically insofar as it does not participate in the reaction. Examples of such solvents are dioxane, 1,2-dimethoxyethane, tetrahydrofuran and like ethers, chloroform, dichloromethane, dichloroethane and like hydrocarbon halides. The reaction is conducted using the latter three reactants each in about 1 to about 3 moles per mole of the compound C. The reaction temperature is −5 to 50° C., preferably about 0° C. to around room temperature. The reaction times is 1 to 15 hours, preferably about 6 to about 12 hours. The compound D resulting from the reaction can be used for the subsequent, reaction, as isolated or without being isolated.

(iv) The compound D is hydrolyzed in a suitable solvent with use of an anion exchange resin to obtain a compound E. The solvent to be used is not limited specifically insofar as it will not participate in the reaction. Examples of such solvents are methanol, ethanol, propanol, isopropanol and like alcohols. The reaction is conducted using the anion exchange resin in about 1 to about 10 moles per mole of the compound D. The reaction temperature is room temperature to 100° C., and the reaction time is about 10 to about 24 hours. The compound E resulting from the reaction can be used for the subsequent reaction, as isolated or without being isolated.

(v) The compound E is reacted with benzyl bromide in a suitable solvent in the presence of a base to obtain a compound F. The solvent to be used is not limited specifically insofar as it does not participate in the reaction. Examples of such solvents are N,N-dimethylformamide, N,N-dimethylacetamide, acetonitrile and like aprotic polar solvents, dioxane, 1,2-dimethoxyethane, tetrahydrofuran and like ethers. Examples of useful bases are trimethylamine, triethylamine, pyridine and like tertiary amines, potassium carbonate, sodium carbonate and like alkali metal carbonate, and potassium hydride, sodium hydride and like alkali metal hydrides. For the reaction, the base and benzyl bromide are used each in about 1 to about 2 moles per mole of the compound E. The reaction temperature is room temperature to 100° C. preferably room temperature to about 70° C. The reaction time is 8 to 30 hours, preferably about 20 to about 28 hours. The compound F resulting from the reaction can be used for the subsequent reaction, as isolated or without being isolated.

(vi) The compound F is subjected to a ketal removing reaction in a suitable solvent with use of an acid to obtain a compound G. The solvent is not limited specifically insofar as it does not participate in the reaction. Examples of solvents are alcohols such as methanol, ethanol, propanol and isopropanol, and ethers such as dioxane, 1,2-dimethoxyethane and tetrahydrofuran. Examples of useful acids are acetic acid, trifluoroacetic acid, oxalic acid and like organic acids, hydrochloric acid, bromic acid, sulfuric acid, nitric acid and like inorganic acids. The reaction temperature is 0 to 60° C. preferably about 10 to about 70° C. The reaction time is about 2 to about 8 hours. The compound G resulting from the reaction can be used for the subsequent reaction, as isolated or without being isolated.

(vii-a) The compound G is reacted with hydroxylamine and sodium acetate in a suitable solvent to obtain an oxime of the compound G. The solvent is not limited specifically insofar as it does not participarte in the reaction. Examples of useful solvents are methanol, ethanol, propanol, isopropanol and like alcohols, dioxane, 1,2-dimethoxyethane, tetrahydrofuran and like ethers. Hydroxylamine and sodium acetate are used each in about 1.5 to 2 moles per mole of the compoudn G. The reaction temperature is 0 to 50° C., preferably room temperature. The reaction time is preferably 5 to 8 hours.

Subsequently, the resulting oxime of the compound G is reacted with p-toluenesulfonyl chloride in a suitable solvent in the presence of a base to obtain a p-tosylic acid ester of the compound G. Silica gel is added to the ester in the same solvent, followed by a Beckmann rearrangement reaction to obtain a mixture of compound Ha and compound Hb. The solvent to be used is not limited specifically insofar as it does not participate in the reaction. Examples of such solvents are benzene, toluene, xylene and like aromatic hydrocarbons, chloroform, dichloromethane, dichloroethane and like hydrocarbon halides. Examples of useful bases are trimethylamine, triethylamine, pyridine and like tertiary amines. For the reaction, the base and p-tosyl chloride are used each in 2 to 3 moles per mole of the oxime of the compound C. The reaction temperature for tosylation is about 0 to 10° C., and the reaction time is about 4 to about 8 hours. The Beckmann rearrangement reaction in silica gel is conducted at a temperature of about 10 to about 30° C. for about 12 to about 24 hours.

(vii-b) The resulting mixture is reacted with a compound I in a suitable solvent in the presence of a base to obtain a compound Ja and compound Jb. The solvent is not limited specifically insofar as it does not participate in the reaction. Examples of useful solvents are chloroform, dichloromethane, dichloroethane and like hydrocarbon halides. Examples of useful bases are tertiary amines such as trimethylamine, triethylamine and pyridine. For the reaction, the base is used in about 1 to about 2 moles per mole of the mixture. The reaction temperature is about 5 to about 50° C., preferably about 10° C. to around room temperature. The reaction time is 12 to 36 hours, preferably about 24 to about 36 hours. The compound Ja or compound Jb resulting from the reaction can be used for the subsequent reaction, as isolated or without being isolated.

(viii) The compound Ja is hydrogenated in a suitable solvent in the presence of palladium-carbon to obtain a compound (1-b). The solvent is not limited specifically insofar as it does not participate in the reaction. Examples of useful solvents are methanol, ethanol, propanol, isopropanol and like alcohols, dioxane, 1,2-dimethoxyethane, tetrahydrofuran and like ethers, and methyl acetate, ethyl acetate and like acetic acid esters. For the reaction, palladium-carbon is used preferably in the ratio of 0.5 to 1 by weight based on the compound Ja. The reaction temperature is preferably around room temperature to about 50° C. The reaction time is about 10 to about 20 hours.

The compound (1) thus obtained can be isolated and purified by a usual method such as recrystallization or column chromatography. The racemic compound obtained can be divided into the desired optical isomers, for example, by fractional recrystallization for the separation of salts from optically active acids or by passing a column packed with an optically active carrier. The stereoisomers can be individually separated off and purified by a usual method such as fractional crystallization or chromatography.

The anxiolytic agent embodying the present invention can be given orally or parenterally to mammals including man. The pharmaceutical preparations of the present invention are not limited specifically in the unit form of administration but can be in various forms in conformity with preventive or therapeutic purposes. These forms of preparations include, for example, oral preparations, injections, suppositories, external preparations (such as poultices and like plasters, ointments, creams and lotions), eye drops, nasal drops or sprays, etc.

The anxiolytic agent of the present invention is prepared and used in the form of a composition having a desired conventional pharmaceutical carrier or excipient incorporated therein by a usual method.

Stated more specifically, examples of carriers for use in formulating the agent as tablets, encapsulated preparations, granules, powders, etc. for oral administration are excipients such as Lactose, sucrose, sodium chloride, glucose, urea, starch, calcium carbonate, kaolin, crystalline cellulose and silicic acid, binders such as water, ethanol, propanol, syrup, glucose solution, starch solution, gelatin solution, carboxymethyl cellulose, hydroxypropyl cellulose, hydroxypropyl starch, shellac, methyl cellulose, ethyl cellulose, potassium phosphate and polyvinylpyrrolidone, disintegrators such as dried starch, sodium alginate, agar powder, laminaria powder, sodium hydrogencarbonate, calcium carbonate, polyoxyethylene sorbitan fatty acid esters, sodium laurylsulfate, stearic acid monoglyceride, starch and lactose, disintegration suppressants such as sucrose, stearic acid, cacao butter and hydrogenated oils, absorption promoters such as quaternary ammonium bases and sodium laurylsulfate, humectants such as glycerin and starch, absorbents such as starch, lactose, kaolin, bentonite and colloidal silicic acid, glazing agents such as purified talc, stearic acid salts, boric acid powder and polyethylene glycol, corrigents such as sucrose, bitter orange peel, citric acid and tartaric acid, etc. When required, the tablets can be those having a usual coating, such as sugar-coated tablets, gelatin-coated tablets, enteric-coated tablets, film-coated tablets, double-layer tablets and multi-layer tablets. The encapsulated preparation is made by mixing the present compound with carriers such as those exemplified above and filling the mixture into hard gelatin capsules or soft capsules.

Liquid preparations for oral administration include aqueous or oily suspensions, solutions, syrups and elixirs, and are prepared in the usual manner by adding a corrigent, buffer, stabilizer, flavoring agent, to the present compound. In this case, examples of useful corrigents are those exemplified above, useful buffers include sodium citrate, and useful stabilizers include tragacanth, gum arabic and gelatin, etc.

Injections are aqueous or oily suspensions and solutions, or powdery fillers and freeze-dried preparations which are dissolved when to be used. Injections are prepared in the usual manner by adding to the present compound a pH adjusting agent, buffer, stabilizer, isotonic agent, diluent, local anesthetic, etc. Examples of pH adjusting agents and buffers for use in this case are sodium citrate, sodium acetate, sodium phosphate and the like. Examples of useful stabilizers are sodium pyrosulfite, EDTA, thioglycolic acid, thiolactic acid, etc. Examples of useful diluents are water, aqueous solution of lactic acid, ethyl alcohol, propylene glycol, ethoxylated isostearyl alcohol, polyoxyisostearyl alcohol, polyoxyethylene sorbitan fatty acid ester, etc. Examples of useful local anesthetics are procaine hydrochloride, lidocaine hydrochloride, etc.

In preparing suppositories, use can be made of carriers such as polyethylene glycol, lanolin, cacao fat, esters of higher alcohols, gelatin, semisynthetic glyceride, etc., and when required, surfactants such as Tween (trademark).

Ointments (pastes, creams, gels, etc.) are prepared by admixing with the present compound a base, stabilizer, lubricant, preservative, etc. which are usually used. Examples of bases are fluid paraffin, white petrolatam, bleached beeswax, octyldodecyl alcohol, paraffin and the like. Examples of useful preservatives are methyl p-hydroxybenzoate, ethyl p-hydroxybenzoate, propyl p-hydroxybenzoate and the like.

Plasters are prepared by applying the ointment, cream, gel, paste or the like to a usual support in the conventional manner. Examples of suitable supports are woven or nonwoven fabrics of cotton, staple fiber or chemical fiber, films of flexible polyvinyl chloride, polyethylene, polyurethane or the like, and foamed sheets of such material.

When required, the foregoing preparations may have further incorporated therein a coloring agent, preservative, perfume, flavoring, sweetener and the like, and other medicinals.

The method of administering the pharmaceutical preparation of the invention is not limited specifically but determined according to the form of preparation, age, sex and other conditions of the patient and degree of symptom of the patient. For example, tablets, pellets, powders, solutions, suspensions, emulsions, granules and capsules are given orally. Suppositories are introduced into the rectum. Injections are intravenously given singly or as mixed with a usual auxiliary solution such as glucose or amino acid solution. Further when required, they are singly administered intra-arterially, intramuscularly, intracutaneously, subcutaneously or intraperitoneally. Ointments are applied to the skin, mucous membrane of the oral cavity, etc. Plasters are applied to the skin.

The dosage of the effective component of the preparation of the invention can be suitably determined according to the mode of administration, age, sex and other conditions of the patient and degree of the symptom. Generally the effective component is administered at a daily dose usually of 0.001 to 10 mg/kg body weight, preferably 0.01 to 5 mg/kg body weight. The present preparation can be given once or in about 2 to about four divided doses per day.

BEST MODE OF CARRYING OUT THE INVENTION

The present invention will be described below with reference to reference examples, examples and test examples. However, the invention is not limited by these examples.

REFERENCE EXAMPLE 1

In 100 ml of dichloromethane were dissolved 3.0 g (19.6 mmol) of 2-azabicyclo[4.4.0]decane-3-one [Journal of American Chemical Society, 77, 409 (1955)], 3.35 g (19.6 mmol) of p-methoxybenzoyl chloride and 2.38 g (23.5 mmol) of triethylamine and the solution was heated under reflux for 2 hours. After cooled, an organic layer was washed with water, % hydrochloric acid and saturated aqueous solution of sodium chloride, and dried over anhydrous magnesium sulfate. After removing the solvent, the resulting residue was chromatographed over silica gel to obtain 4.5 g (yield 80%) of 2-(4-methoxybenzoyl)-2-azabicycLo[4.4.0]decane-3-one (Compound 1) from hexane-ethyl acetate (3:1) eluate. Table 1 shows melting point and yield of the compound.

REFERENCE EXAMPLE 2

Compound 2 was obtained in the same manner as in Reference Example 1 with use of, as a starting material, 2-azabicyclo[3.3.0]octane-3-one (Yakugaku Zasshi, 84, 674 (1964)). Table 1 shows melting point and yield of the compound.

REFERENCE EXAMPLE 3

A known compound, 2-azabicyclo[4.3.0]nonane-3-one was prepared by the method disclosed in Journal of American Chemical Society, 77, 409 (1955).

Namely, to a solution of 50 ml (0.35 mol) of ethyl cyclopentanone-2-carboxylate in 130 ml of dioxane was added 3.8 ml of Triton B. Then, to the solution was added 27.1 ml (0.242 mol) of acrylonitrile in 50 ml of dioxane. The solution was stirred at room temperature tor 12 hours, and extracted with ether after 100 ml of 10% hydrochloric acid was added thereto. An organic lay(er was dried over anhydrous magnesium sulfate. After removing the solvent, 300 ml of conc. hydrochloric acid was added to the residue and the mixture was heated under reflux for 24 hours. After cooling, the mixture was extracted with ether and 5% aqueous solution of sodium hydroxide was added to the ether layer and the mixture was stirred. An aqueous layer was made acidic with addition of 10% hydrochloric acid, and then the mixture was extracted with ethyl acetate. An organic layer was dried over anhydrous magnesium sulfate. After removing the solvent, the residue was dissolved in 150 ml of ethanol and 10 ml of conc. sulfuric acid was added thereto. The mixture was heated under reflux for 14 hours, and then ethanol was removed therefrom after cooling, and ethyl acetate was added thereto. The mixture was washed with 10% aqueous solution of sodium hydroxide and dried over anhydrous magnesium sulfate. After removing the solvent, the resulting residue was chromatographed over silica gel to obtain 45 g (yield 70%) of ethyl 2-oxocyclopentanepropionate from hexane-ethyl acetate (4:1) eluate. In 150 ml of 80% ethanol was dissolved 5.5 g (30 mmol) of this compound. To the solution were added 4.17 g (60 mmol) of hydroxylamine hydrochloride and 2.7 g (33 mmol) of sodium acetate and the mixture was stirred at room temperature over night. After removing ethanol, the mixture was extracted with ethyl acetate and dried over anhydrous magnesium sulfate. After removing the solvent, the resulting residue was chromatographed over silica gel to obtain 5 g (yield 84%) of ethyl 2-hydroxyiminocyclopentanepropionate from hexane-ethyl acetate (6:1) eluate. In 15 ml of anhydrous ethanol was dissolved 4.4 g of this compound and the solution was stirred at 50° C. for 4 hours under a hydrogen pressure of 120 atm. with use of Raney nickel (W2) as a catalyst. After removing Raney nickel by filtration and removing the solvent, the resulting residue was chromatographed over silica gel to obtain 0.95 g (yield 31%) of 2-azabicyclo[4.3.0]nonane-3-one from ethyl acetate eluate.

Compounds 3 to 10 were obtained in the same manner as in Reference Example 1 with use of the above compound as a starting material.

REFERENCE EXAMPLE 4

A known compound, 7-azabicyclo[4.3.0]nonane-8-one was prepared by the method disclosed in Yakugaku Zasshi, 84, 674 (1964).

Namely, the desired 7-azabicyclo[4.3.0]nonane-8-one was prepared in the same manner as in Reference Example 3, with use of, as a starting material, ethyl 2-oxocyclohexyl acetate.

Compound 11 was obtained in the same manner as in Reference Example 1 with use of the above compound as a starting material.

REFERENCE EXAMPLE 5

Compound 12 was obtained in the same manner as in Reference Example 1 with use of, as a starting material, 8-azabicyclo[4.3.0]nonane-7-one [Journal of Chemical Society Perkin Transactions I 11, 2563 (1982)]. Table 1 shows melting point and yield of the compound.

In Table 1, Me and OMe stand for methyl and methoxy respectively.

TABLE 1
| No. | l | m | n | R | m.p. (° C.) | yield (%) | formula |
|---|---|---|---|---|---|---|---|
| 1 | 2 | 0 | 2 | 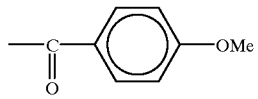 | 90~91 | 80 | $C_{17}H_{21}NO_3$ |
| 2 | 1 | 0 | 1 | 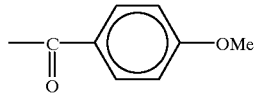 | 63~64 | 65 | $C_{15}H_{17}NO_3$ |
| 3 | 1 | 0 | 2 | 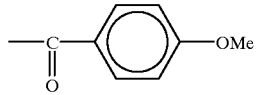 | oil | 80 | $C_{16}H_{19}NO_3$ |
| 4 | 1 | 0 | 2 | 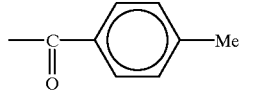 | 79~80 | 82 | $C_{16}H_{19}NO_2$ |
| 5 | 1 | 0 | 2 | 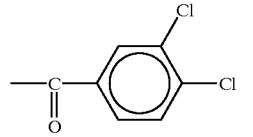 | 82~83 | 90 | $C_{15}H_{15}NO_2Cl_2$ |
| 6 | 1 | 0 | 2 | 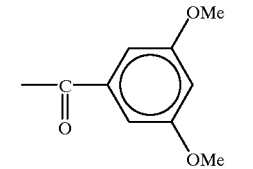 | 78.5~79.5 | 81 | $C_{17}H_{21}NO_4$ |
| 7 | 1 | 0 | 2 | 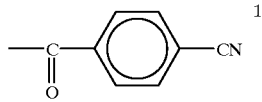 | 148.5–149 | 83 | $C_{16}H_{16}N_2O_2$ |
| 8 | 1 | 0 | 2 | 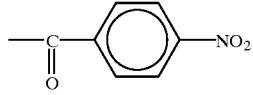 | 148~149 | 85 | $C_{15}H_{16}N_2O_4$ |
| 9 | 1 | 0 | 2 | 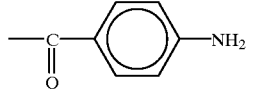 | 132~134 | 65 | $C_{15}H_{18}N_2O_2 \cdot \frac{1}{2}H_2O$ |
| 10 | 1 | 0 | 2 | 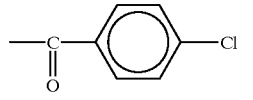 | 100~101 | 90 | $C_{15}H_{16}NO_2Cl$ |
| 11 | 2 | 0 | 1 | 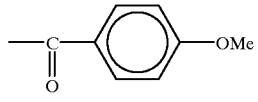 | oil | 79 | $C_{16}H_{19}NO_3$ |
| 12 | 2 | 1 | 0 | 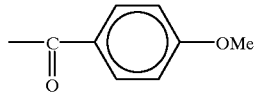 | 67~69 | 52 | $C_{16}H_{19}NO_3$ |

REFERENCE EXAMPLE 6

Preparation of 6-oxo-bicyclo[3.3.0]octan-2-one=ethylene=acetal (Compound B)

A 9.62 g quantity of bicyclo[3.3.0]octan-2,6-dione (Compound A), 0.265 g of p-toluenesulfonic acid monohydrate and 4.54 g of ethylene glycol were dissolved in 50 ml of benzene, and the mixture was refluxed for reaction for 6 hours while removing water as an azeotropic mixture. After the reaction, the mixture was cooled to room temperature and allowed to stand for 15 minutes with addition of 3 g of sodium hydrogencarbonate. The resulting precipitate was filtered off and washed with benzene. The filtrate was concentrated to obtain a brown oily product, which was purified by column chromatography using 180 g of silica gel and hexane-ethyl acetate (5:1) to obtain 9.28 g of Compound B mentioned above in the form of a colorless oily substance (yield: 73%).

$^1$H-NMR (CDCl$_3$) δ ppm: 1.80~2.45 (m, 10H), 3.95(s, 4H)

REFERENCE EXAMPLE 7

Preparation of γ-1,t-2-hydroxybicyclo[3.3.0]octan-6-one=ethylene=acetal (Compound C)

A 9.23 g quantity of Compound B obtained in Reference Example 6 was dissolved in 70 ml of methanol, and 1.93 g of sodium boron hydride was added to the solution while cooling the solution ir an ice-methanol bath. The mixuture was returned to room temperature 30 minutes later, followed by further reaction for 1 hour. The methanol was thereafter distilled off, 70 ml of water was added to the residue, and the mixture was subjected to extraction with 100 ml of dichloromethane and 50 ml of dichloromethane twice. The dichloromethane layer obtained was washed with 50 ml of saturated aqueous sodium chloride solution, then dried over anhydrous sodium sulfate and distilled for the removal of solvent, giving a colorless oily product. The product was purified by column chromatography using 150 g of silica gel and hexane-ethyl acetate (4:1 to 2:1) to obtain 6.63 g of Compound C mentioned above in the form of a colorless oily substance (yield: 71%).

$^1$H-NMR (CDCl$_3$) δ ppm: 1.75~2.00(m, 8H), 2.10~2.80 (m, 2H), 3.90~4.18 (m, 1H), 3.94(s, 4H)

REFERENCE EXAMPLE 8

Preparation of γ-1,c-2-(4-nitrobenzoyloxy)bicyclo-[3.3.0]octan-6-one=ethylene=acetal (Compound D)

A 3.68 g quantity of Compound C obtained in Reference Example 7, 6.68 g of p-nitrobenzoic acid and 10.5 g of triphenylphosphine were dissolved in 70 ml of tetrahydrofuran, and a solution of 7.00 g of diethyl azodicarboxylate in 10 ml of tetrahydrofuran was added dropwise to the solution with ice cooling over a period of 10 minutes. The mixture was stirred with ice cooling for 1 hour, then returned to room temperature and further reacted for 16 hours. The solvent was distilled off from the reaction mixture, 50 ml of ether and 30 ml of hexane were added to the residue, and the resulting mixture was allowed to stand in a refrigerator for 1 day. The resulting precipitate (triphenylphosphine oxide) was filtered off and washed with hexane-ether (2:1). The filtrate obtained was concentrated to obtain a yellow oily product. The product was purified by column chromatography using 90 g of silica gel, hexane and hexane-ethyl acetate (10:1), giving 5.34 g of Compound D mentioned above in the form of a light yellow oily substance (yield: 80%).

$^1$H-NMR (CDCl$_3$) δ ppm: 1.60~2.20(m, 8H), 2.45~2.90 (m, 2H), 3.94(s, 4H), 5.10~5.23(m, 1H), 8.24(s, 4H)

REFERENCE EXAMPLE 9

Preparation of γ-1,c-2-hydroxybicyclo[3.3.0]octan-6-one=ethylene=acetal (Compound E)

A 12.85 g quantity of Compound D obtained in Reference Example 8 was dissolved in 100 ml of methanol, 15 g of an anion exchange resin, Amberlite IR400 (OH—) (product of Organo Co., Ltd.), was added to the solution, and the mixture was refluxed for 8 hours. Since the starting material still remained, 10 g of the anion exchange resin was further added to the mixture, followed by refluxing for 16 hours. The reaction mixture was returned to room temperature, filtered under High Flow Supercell (product of Nacalai Tesque Co., Ltd.) and washed with methanol. Filtration gave a filtrate, which was concentrated and purified by column chromatography using 100 g of silica gel and hexane-ethyl acetate (3:1), whereby 6.52 g of Compound E abovementioned was obtained as a colorless oily substance (yield: 92%).

$^1$H-NMR (CDCl$_3$) δ ppm: 1.20~2.15 (m, 8H), 2.30~2.80 (m, 2H) 3.80~4.10(m, 1H), 3.91(s, 4H)

REFERENCE EXAMPLE 10

Preparation of γ-1,c-2-benzyloxybicyclo[3.3.0]-octan-6-one=ethylene=acetal (Compound F)

A 6.40 g quantity of Compound E obtained in Reference Example 9 was; dissolved in 40 ml of N,N-dimethylformamide, 2.08 g of 60% sodium hydride was added to the solution, and the mixture was stirred at room temperature. The reaction temperature rose to about 45° C. with evolution of hydrogen. One hour later, the reaction mixture was cooled with ice, followed by addition of 6.3 ml of benzyl bromide. The mixture was returned to room temperature 30 minutes thereafter and stirred for 24 hours, followed by further reaction on a bath of 70° C. for 4 hours. The mixture was returned to room temperature, and 80 ml of ice water was added thereto. The resulting mixture was subjected to extraction with 60 ml of ether three times. The ethereal layer was washed with 20 ml of water three times and with 20 ml of saturated aqueous solution of sodium chloride and thereafter dried over anhydrous sodium sulfate. Removal of the solvent from the layer gave an oily product, which was then purified by column chromatography using 75 g of silica gel, and hexane and hexane-ether (15:1), whereby 6.65 g of Compound F mentioned above was obtained as an oily substance (yield: 70%).

$^1$H-NMR (CDCl$_3$) δ ppm: 1.60~2.10(m, 8H), 2.40~2.80 (m, 2H) 3.50~3.80(m, 1H), 3.90(s, 4H), 4.92(s, 2H), 7.31(s, 5H)

REFERENCE EXAMPLE 11

Preparation of γ-1,c-2-benzyloxybicyclo[3.3.0]-octan-6-one (Compound G)

A 1.94 g quantity of Compound F obtained in Reference Example 10 was dissolved in 10 ml of tetrahydrofuran, and the solution was stirred for 6 hours with 3 ml of 2N hydrochloric acid added thereto. The tetrahydrofuran was distilled off from the resulting reaction mixture, followed by extraction with 20 ml of ether twice. The ethereal layer was washed with 10 ml of saturated aqueous solution of sodium hydrogencarbonate twice and then with 5 ml of saturated aqueous solution of sodium chloride, and dried over anhydrous sodium sulfate. Removal of the solvent from the layer give 1.60 g of Compound G mentioned above as an oily substance (yield: 98%).

$^1$H-NMR (CDCl$_3$) δ ppm: 1.30~2.40(m, 8H), 2.60~3.00 (m, 2H), 3.70~3.90(m, 1H), 4.51(s, 2H), 7.33(s, 5H)

REFERENCE EXAMPLE 12

Preparation of γ-6,c-7-benzyloxy-2-(4-methoxybenzoyl)-2-azabicyclo[4.3.0]nonan-3-one (Compound Ja) and γ-6,c-7-benzyloxy-3-(4-methoxybenzoyl)-3-azabicyclo-[4.3.0]nonan-2-one (Compound Jb)

A 1.54 g quantity of Compound G obtained in Reference Example 11 was dissolved in 15 ml of tetrahydrofuran, followed by addition of 8 ml of water and thereafter by addition of 0.94 g of hydroxylamine hydrochloride and 1.84 g of sodium acetate trihydrate. Tetrahydrofuran was subsequently added to obtain a homogeneous mixture, which was then stirred at room temperature for 5 hours. The tetrahydrofuran was distilled off from the reaction mixture, followed by extraction with 80 ml of ethyl acetate. The ethyl acetate layer was washed with 10 ml of water, with ml of saturated sodium hydrogencarbonate solution and subsequently with 10 ml of saturated aqueous solution of sodium chloride, and thereafter dried over anhydrous sodium hydrogen sulfate. Distillation of the layer for the removal of the solvent gave 1.64 g of oxime of Compound G as a colorless oily substance.

A 1.60 g of the oxime obtained was dissolved in 16 ml of benzene, followed by addition of 3.11 g of p-toluenesulfonyl chloride and then by addition of 2.27 ml of triethylamine with ice cooling. The mixture was stirred for 4 hours with ice cooling and subsequently for 2 hours at room temperature, and thereafter diluted with 50 ml of ether. The resulting solution was washed with 10 ml of water, with 10 ml of 2N hydrochloric acid twice and subsequently with 10 ml of saturated aqueous solution of sodium chloride, and thereafter dried over anhydrous sodium sulfate. Removal of the solvent from the solution gave a yellow oily product. The product was dissolved in 50 ml of anhydrous benzene, followed by addition of 43 g of silica gel (Fuji Silysia Chemical Ltd., BW-300 as washed with 2N HCl and then thoroughly with water, and dried at 230° C. for 16 hours) and further by addition of anhydrous benzene in an amount of permitting stirring of the resulting mixture. The mixture was shaken on a water bath having a constant temperature of 25° C. for 18 hours. The reaction mixture was poured into a column packed with 20 g of silica gel, and 300 ml of benzene was passed through the column to cause an excess of p-toluenesulfonyl chloride to flow out. The solvent was thereafter changed for benzene-methanol (6:1) to obtain an eluate. The eluate still contained impurities and was therefore purified by column chromatography again using 30 g of silica gel, and chloroform and chloroform-methanol (50:1). The product was dried in a vacuum at room temperature to obtain 1.233 g of a light yellow oily substance. PMR analysis revealed that the product was a mixture of γ-6,c-7-benzyloxy-2-azabicyclo[4.3.0]nonan-3-one (Compound Ha) and γ-6,c-7-benzyloxy-3-azabicyclo[4.3.0]nonan-2-one (Compound Hb) approximately in the ratio of 2:1.

The mixture (1.18 g) obtained was dissolved in 15 ml of dichloromethane, 1.31 g of p-methoxybenzoyl chloride and 1.34 g of triethylamine were added to the solution, and the mixture was stirred at room temperature for 36 hours. With addition of 80 ml of ethyl acetate, the reaction mixture was washed with 20 ml of 2N hydrochloric acid twice, with 20 ml of saturated solution of sodium hydrogencarbonate twice and then with 10 ml of saturated aqueous solution of sodium chloride, and dried over anhydrous sodium sulfate. Removal of the solvent gave a brown oily product, which was then purified by column chromatography using 30 g of silica gel and hexane-ethyl acetate (4:1 to 3:1). The component eluted first was Compound Jb mentioned above and obtained in an amount of 0.576 g as a yellow oily substance (yield: 25%). The component eluted thereafter was Compound Ja mentioned above. The fraction was distilled for the removal of the solvent and recrystallized from ethanol, giving 1.05 g of the compound (yield: 46%).

Chracteristic Values of Compound Ja m.p. (in ethanol solvent): 108.5~109.5° C. $^1$H-NMR (CDCl$_3$) δ ppm: 1.30~2.70(m, 10H), 3.70~4.00(m, 1H), 3.83(s, 3H), 4.54(s, 211), 6.87(d, 2H), 7.34(s, 5H), 7.58(d, 2H)

Chracteristic Values of Compound Jb $^1$H-NMR (CDCl$_3$) δ ppm: 1.30~3.30(m, 10H), 3.60~4.10 (m, 1H), 3.83(s, 3H), 4.52(s, 211), 6.86(d, 2H), 7.33(s, 5H), 7.54 (d, 2H)

REFERENCE EXAMPLE 13

γ-6,c-7-Hydroxy-2-(4-methoxybenzoyl)-2-azabicyclo-[4.3.0]nonan-3-one (Compound 13)

A 1.05 g quantity of Compound Ja obtained in Reference Example 12 was dissolved in 15 ml of dioxane, 0.50 g of 10% palladium carbon (product of Wako Junyaku Co., Ltd.) was added to the solution, and the air in the reactor was removed by an aspirator and replaced by hydrogen repeatedly twice. The mixture was thereafter stirred in the hydrogen atmosphere (1 atm.) for 16 hours. The catalyst was filtered off and washed with dioxane. The resulting filtrate was concentrated to obtain a colorless oily product, which was then purified by column chromatography using 15 g bf silica gel and chloroform. Removal of the solvent from the product afforded crystals, which were further recrystallized from ether, giving 0.64 g of Compound 13 mentioned above in the form of a colorless powder (yield: 81%).

m.p. (in diethyl ether solvent) : 120~121° C. $^1$H-NMR (CDCl$_3$) δ ppm: 1.20~2.70(m, 10H), 3.84(s, 3H) 3.90~4.30 (m, 1H), 4.20 (q, 1H), 6.88 (d, 2H), 7.59 (d, 2H)

Example 1

Tablet

| | |
|---|---|
| Compound 1 | 30 mg |
| Microcrystalline cellulose | 50 mg |
| Hydroxypropyl cellulose | 20 mg |
| Lactose | 47 mg |
| Talc | 2 mg |
| Magnesium stearate | 1 mg |

By the usual method, the above ingredients in the proportions given were made into tablets each weighing 150 mg.

Example 2

| Granule | |
|---|---|
| Compound 3 | 10 mg |
| Lactose | 400 mg |
| Corn starch | 370 mg |
| Hydroxypropyl cellulose | 20 mg |

The above ingredients in the proportions given were made into a granular preparation by the usual method in an amount of 800 mg per wrapper.

Example 3

| Capsule | |
|---|---|
| Compound 11 | 55 mg |
| Lactose | 50 mg |
| Corn starch | 50 mg |
| Microcrystalline cellulose | 94 mg |
| Magnesium stearate | 1 mg |

By the usual method, the above ingredients in the proportions given were made into a capsule in an amount of 250 mg in each capsule.

Example 4

| Injection | |
|---|---|
| Compound 13 | 10 mg |
| Sodium chloride | 3.5 mg |

Distilled water for injections, suitable amount

The above ingredients in the proportions given were made into an injection by the usual method.

Example 5

| Syrup | |
|---|---|
| Compound 3 | 50 mg |
| Purified sucrose | 60 g |
| Ethyl para-hydroxybenzoate | 5 mg |
| Butyl para-hydroxybenzoate | 5 mg |
| Perfume | suitable amount |
| Coloring agent | suitable amount |
| Purified water | suitable amount |

The above ingredients in the proportions given were made into a syrup by the usual method.

Example 6

| Suppositories | |
|---|---|
| Compound 11 | 50 mg |
| Witepsol W-35 | 1400 mg |

(Trademark, a mixture of mono-, di- and triglyceride of saturated fatty acids from lauric acid to stearic acid, Dynamite Nobel Co., Ltd.)

By the usual method, the above ingredients in the proportions given were made into suppositories.

TEST EXAMPLE 1

Anticonflict Test

1. Experimental animals

Wistar rats (males weighing 140 to 160 g) were used for experiment in groups of 11 to 14.

2. Test agents and administration method

The test compound, diazepam or buspirone was suspended in a 0.5% sodium carboxymethyl cellulose solution, and the suspension was orally given to the animal in a volume of 5 ml/kg one hour before the start of experiment.

3. Experimental method and result

With reference to a method described in "Process in Anxiolytics and Antidepressants," edited by Showa Ueki and Tatsuo Furukawa, Ishiyaku Shuppansha, 56~59 (1981), the agents were tested using experimental boxes having a grid floor and a metal drinking tube in the floor. No water was supplied to the rats for 48 hours before the experiment. Upon lapse of first 24 hours, each group of rats were placed into the experimental box, permitted access to water for 30 seconds and caused to recognize the metal drinking tube. Upon lapse of further 24 hours with access to water prevented, the rats were placed into the bob again and permitted access to water on condition that an electric current was passed between the metal drinking tube and the grid to give an electroshock for every 20 times of water drinking behavior to measure the frequency of water drinking behavior for 3 minutes. Table 2 shows the result. Compound 1, 3, 11 and 13 exhibited an increase in the frequency of water drinking behavior at doses of 0.001 to 1.0 mg/kg, producing an anxiolytic effect, but diazepam and buspirone were found almost ineffective.

TABLE 2

Anticonflict Test

| Test compound | Dose (mg/kg) | Frequency of water drinking behavior (times/3 min) |
|---|---|---|
| Control | | 100 |
| Compound 1 | 0.01 | 138 |
| | 0.1 | 140 |
| | 1.0 | 122 |
| Compound 3 | 0.001 | 126 |
| | 0.01 | 162 |
| | 0.1 | 164 |
| | 1.0 | 166 |
| Compound 11 | 1.0 | 133 |
| Compound 13 | 0.001 | 130 |
| | 0.01 | 183 |
| | 0.1 | 177 |
| | 1.0 | 169 |
| Diazepam | 1.0 | 96 |
| Buspirone | 1.0 | 103 |

The frequency is expessed by a value relative to the frequency of the control which is taken as 100.

TEST EXAMPLE 2

Elevated Plus Maze Test

1. Experimental animals

Wistar rats (males weighing 170 to 220 g) were used for experiment in groups of 4 to 9.

2. Test agents and administration method

The test compound, diazepam or buspirone was suspended in a 0.5% sodium carboxymethyl cellulose solution, and the suspension was orally given to the animal in a volume of 5 ml/kg one hour before the start of experiment.

3. Experimental method and result

The test was conducted using an experimental device, Model BTA-2, Behavior Analysis System (product of Muromachi Kikai Co., Ltd.) with reference to a method described in Psychopharmacology, 99, 48~53(1989). The device had a maze comprising pairs of opposed open arms having no side walls and positioned at a level of about 50 cm above the floor, closed arms having side walls and a center square at an intersection. Each group of rats orally given the test drug were placed in the center square, and the behavior of the animals was recorded for 5 minutes using a behavior analyzer. The ratio of the number of entries into the open arm to the number of entries into all the arms was determined for evaluating the anxiolytic effect. Table 3 shows the result. Compound 3 achieved an increase in the number of entries into the open arm with lapse of time when taken at a dose of 0.001 mg/kg or greater, thus exhibiting an anxiolytic effect.

TABLE 3

Elevated Plus Maze Test

| Test compound | Dose | Ratio of entries into open arm |
| --- | --- | --- |
| Control |  | 100 |
| Compound 3 | 0.001 | 195 |
|  | 0.01 | 219 |
|  | 0.1 | 248 |
| Diazepam | 1.0 | 103 |
|  | 10.0 | 144 |
| Buspirone | 1.0 | 98 |
|  | 10.0 | 93 |

The ratio of entries into the open arm is expressed by a value relative to the ratio attained by the control which is taken as 100.

TEST EXAMPLE 3

Muscle Relaxant Effect (Traction Method)

1. Experimental animals and administration method

Compound 3, Compound 13, diazepam or buspirone was suspended in a 0.5% sodium carboxymethyl cellulose solution, and the suspension was orally administered to 3- to 4-week-old male ddY mice (in groups of 5) in a volume of 10 ml/kg one hour before the start of experiment.

2. Experimental method and result

With reference to a method described in Japan. J. Pharmacol., 49. 337~349(1989), the foreleg of the mouse was hung on a horizontal wire, having a diameter of 1.2 mm and fixed at a level of 30 cm, three times consecutively. If the hind leg did not touch the wire within 10 seconds each time, the result was interpreted as positive. Thus, $ED_{50}$ was determined for evaluation. Consequently, Compounds 3 and 13 exhibited no muscle relaxant effect even when given at a dose of 300 mg/kg. Diazepam and buspirone were 2.2 mg/kg and 427.6 mg/kg, respectively, in $ED_{50}$.

TEST EXAMPLE 4

Sedative Effect (Spontaneous Locomotor Activity)

1. Experimental animals and administration method

Compound 3, Compound 13, diazepam or buspirone was suspended in a 0.5% sodium carboxymethyl cellulose solution, and the suspension was orally administered to 3- to 4-week-old male ddY mice (in groups of 5) in a volume of 10 ml/kg one hour before the start of experiment.

2. Experimental method and result

The test was conducted with reference to a method described in "Evaluation of Medicinal Efficacies (1), Pharmacological Test Method (I), Basic Lectures on Development of Pharmaceuticals," 50~54(1971). More specifically, the group of mice were given the test drug and thereafter measured the amount of spontaneous locomotor activity for 10 minutes per mouse using Animex MK-110 (product of Muromachi Kikai Co., Ltd.). When the amount of activity was up to 50% of the control group, the result was interpreted as positive to determine $ED_{50}$ for evaluation. Consequently, Compounds 3 and 13 exhibited no sedative effect even at a dose of 300 mg/kg. Diazepam and buspirone were 1.7 mg/kg and 149.7 mg/kg, respectively, in the above value.

TEST EXAMPLE 5

Effect on Central Nervous System Depressant a. Pentobarbital anesthetic animal

1. Experimental method and administration method

Compound 3, Compound 13, diazepam or buspirone was suspended in a 0.5% sodium carboxymethyl cellulose solution, and the suspension was orally administered to 3- to 4-week-old male ddY mice (in groups of 5 to 10) in a volume of 10 ml/kg one hour before the start of experiment.

2. Experimental method and result

The test was conducted with reference to a method described in "Evaluation of Medicinal Efficacies (1), Pharmacological Test Method (I), Basic Lectures on Development of Pharmaceuticals," 144~145(1971). More specifically, the group of mice were intraperitoneally given pentobarbital at a dose of 40 mg/kg and checked for sleeping time. When the sleeping time was in excess of twice that of the control group, the result was interpreted as positive to determine $ED_{50}$ for evaluation. Consequently, Compound 3 was at least 300 mg/kg, and Compound 13 was 224.5 mg/kg in this value. Diazepam and buspirone were 0.53 mg/kg and 91.7 mg/kg, respectively, in the value.

b. Ethanol enhancing method

1. Experimental animals and administration method

Compound 3, Compound 13, diazepam or buspirone was suspended in a 0.5% sodium carboxymethyl cellulose solution, and the suspension was orally administered to 3- to 4-week-old male ddY mice (in groups of 6) in a volume of 10 ml/kg one hour before the start (of experiment.

2. Experimental method and result

The test was conducted with reference to a method described in Japan. J. Pharmacol., 49, 337~349(1989). More specifically, the group of mice were intraperitoneally given 25% ethanol at a dose of 20 ml/kg and checked for the time interval between loss and recovery of the righting reflex. When the time measurement was in excess of twice the measurement of the control group, the result was interpreted as positive to determine $ED_{50}$ for evaluation. Consequently, Compounds 3 and 13 produced no ethanol enhancing effect even at a dose of 300 mg/kg. Diazepam and buspirone were 0.48 mg/kg and 120.1 mg/kg, respectively, in the value.

TEST EXAMPLE 6

Anticonvulsant Effect (Pentylenetetrazol-induced Convulsion Method)

1. Experimental animals and administration method

Compound 3, Compound 13, diazepam or buspirone was suspended in a 0.5% sodium carboxymethyl cellulose solution, and the suspension was orally administered to 3- to 4-week-old male ddY mice (in groups of 6) in a volume of 10 ml/kg one hour before the start of experiment.

2. Experimental method and result

The test was conducted with reference to a method described in "Evaluation of Medicinal Efficacies (1), Pharmacological Test Method (I), Basic lectures on Development of Pharmaceuticals," 167~172(1971). More specifically, pentylenetetrazol was subcutaneously administered to the mouse at a dose of 150 mg/kg, and when the mouse did not die due to onset of convulsion within 60 minutes, the result was interpreted as positive to determine $ED_{50}$ for evaluation. Consequently, Compounds 3 and 13 exhibited no anticonvulsant effect even at a dose of 300 mg/kg. Diazepam and buspirone were 0.35 mg/kg and at least 300 mg/kg, respectively, in the value.

TEST EXAMPLE 7

Acute Toxicity Test

Five-week-old male ddY mice were used in groups of 4 to 5. The mice were orally given the test compound as suspended in a 0.5% sodium carboxymethyl cellulose solution and thereafter observed for 3 days to measure the number of deaths and determine $LD_{50}$. Table 4 shows the result.

TABLE 4

Acute Toxicity Test

| Test compound | Acute Toxicity $LD_{50}$ (mg/kg) |
|---|---|
| Compound 1 | 2000< |
| Compound 3 | 2000< |
| Compound 11 | 2000< |
| Compound 13 | 3000< |

INDUSTRIAL APPLICABILITY

The anxiolytic agent comprising a bicyclolactam derivative represented by the formula (1) as its effective component has a high anxiolytic effect, is reduced in side effects such as sedative, muscle relaxant, hypnotic and anticonvulsant effects and is low in toxicity. Accordingly, the agent of the present invention is useful for treating or preventing chronic or acute anxiety disorders (or anxiety and fear neuroses), such as panic disorder accompanied or not accompanied by agoraphobia, social phobia or simple phobia, obsessive-compulsive disorder (neurosis), stress disorder resulting from injury and systemic anxiety disorder, and other anxiety disorders, and also for relieving healthy persons and the aged of anxiety.

Additionally, the present invention is useful for treating or preventing the anxiety attendant on withdrawal symptoms due to drug dependence and/or drug addiction. Thus, the present invention is useful for allaying withdrawal symptoms due to alcohol dependence, nicotine dependence, cocaine dependence and benzodiazepine dependence and withdrawal symptoms due to other drug dependence.

The present invention also relates to a novel bicyclolactam compound, use thereof and an intermediate for preparing the bicyclolactam compound. The present compound has an excellent anxiolytic effect and is useful as an anxiolytic agent.

The compounds which are similar to the bicyclolactam compounds of the present invention are disclosed in International Publication No. WO 91/11434, and are known to have a cerebral function improving effect, cerebral metabolism activating or anoxic brain damage protecting effect and effect against senile dementia. The present compound differs from those disclosed in WO 91/11434 in that the former has a substituent ring directly attached to a carbon atom on the bicyclo ring.

Further, when the compound disclosed in International Publication No. WO 91/11434 is orally administered, a lot of metabolites are produced. This causes an administration of non-effective substances and is unsuitable to develop pharmaceuticals. The present compound produces less amount of metabolites and is high in safety.

An object of the present invention is to provide a novel bicyclolactam compound and an intermediate for production of the bicyclolactam compound. The bicyclolactam compound has an excellent anxiolytic effect, is high in safety and is useful as an effective component of medicinals which are greatly diminished in side effects such as hypnotic, muscle relaxant and sedative effects.

DISCLOSURE OF THE INVENTION

The present invention provides a bicyclolactam compound represented by the following formula (1)

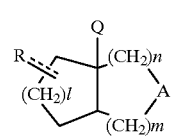

(1)

wherein R is oxo or —$OR^1$, $R^1$ is a hydrogen atom or acyl group, A is a group of (2) or (3), Q is a hydrogen atom or lower alkyl group, l is 1 or 2, m is 0 or 1 and n is 0, 1 or 2, provided the case where both of m and n represent 0 simultaneously is excluded

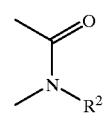

(2)

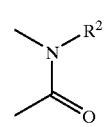

(3)

wherein $R^2$ is benzoyl group or substituted benzoyl group.

The present invention also provides a bicyclolactam compound represented by the following formula (4)

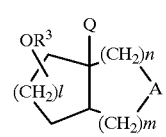

(4)

wherein A, Q, l, m and n are as defined above, $R^3$ is benzyl group or substituted benzyl group.

The present invention further provides a process for preparing a bicyclolactam compound represented by the following formula (1'), comprising replacing $R^3$ in the bicyclolactam compound of the formula (4) by hydrogen atom in a suitable solvent in the presence of a catalyst

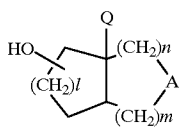
(1′)

wherein A, Q, l, m and n are as defined above.

The present invention further provides a process for preparing a bicyclolactam compound represented by the following formula (1″), comprising acylating the bicyclolactam compound of the formula (1′) in a suitable solvent

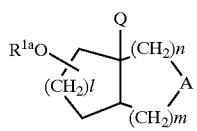
(1″)

wherein A, Q, l, m and n are as defined above, $R^{1a}$ is acyl group.

The present invention further provides a process for preparing a bicyclolactam compound represented by the following formula (1‴), comprising reacting a compound of the formula (5) and a bicyclolactam compound of the formula (6) in a suitable solvent in the presence of a base $$R^2-X \quad (5)$$

wherein $R^2$ is as defined above, X is a halogen atom,

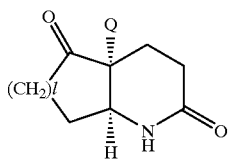
(6)

wherein Q and l are as defined above,

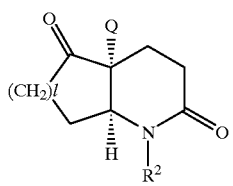
(1‴)

wherein $R^2$, Q and l are as defined above.

The present invention further provides a pharmaceutical composition comprising an effective amount of the above bicyclolactam compound and a pharmaceutically acceptable carrier.

The present invention further provides an anxiolytic agent comprising an effective amount of the above bicyclolactam compound and a pharmaceutically acceptable carrier.

The present invention further includes a method of treating anxiety comprising administering an effective amount of the above bicyclolactam compound to mammals including man, and also use of the above bicyclolactam compound for the preparation of medicinals for treating anxiety.

The bicyclolactam compound of the formula (1) has an excellent anxiolytic effect, is high in safety, diminished in side effects, and useful as medicinals. Further, the bicyclolactam compound of the formula (4) is useful as an intermediate for preparing the bicyclolactam compound of the formula (1).

Existing as bicyclolactam derivatives of the formula (1) or (4) are stereoisomers due to the presence of the bicyclo ring, and also geometric isomers and optical isomers due to the presence of the carbon atom at the bridgehead position of the bicyclo ring and the carbon atom having $R^1O-$ or $R^3O-$ attached thereto. The present invention includes all of these isomers.

In view of the numbers l, m and n, the following fourteen (14) kinds of bicyclo ring skeletons can be present in the compounds of the formula (1) or (4). The invention includes all of these cases.

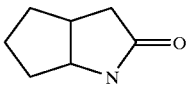
(a)

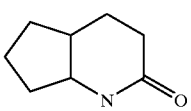
(b)

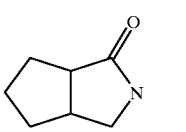
(c)

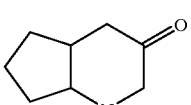
(d)

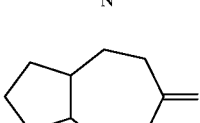
(e)

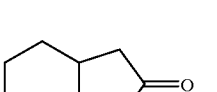
(f)

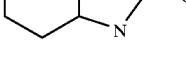
(g)

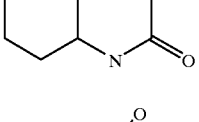
(h)

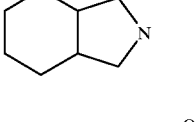
(i)

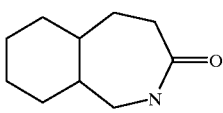
(j)

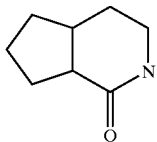
(k)

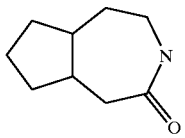
(l)

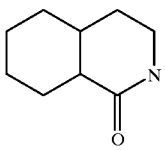
(m)

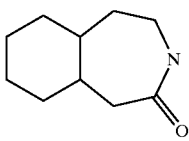
(n)

Preferable among these is the case wherein m or n is 0, i.e. the skeleton (a), (b), (c), (f), (g), (h), (k) or (m) More preferable is the case wherein l is 1, m is 0, n is 2, i.e., (b) or (k).

In the present invention, in the case where the substituent R is oxo group, the bond between R and the carbon on the bicyclo ring shows double bond.

In case of, for example, the above bicyclolactam ring skeleton (a), the following three positions are shown where the substituent R of the compound of the formula (1) [or —OR$^3$ of the compound of the formula (4)] attaches to the bicyclolactam ring. Although the invention includes all of these cases, preferable is (p) or (r) below where R (or —OR$^3$) attaches to the vicinal carbon atom of the brigehead atom of the bicyclolactam ring. This is similar in the other bicyclolactam ring skeletons (b) to (n).

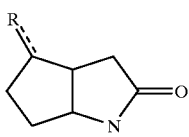
(p)

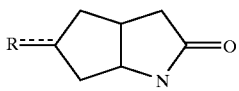
(q)

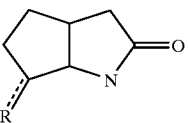
(r)

According to the invention, examples of benzoyl groups which may optionally have at least one substituent represented by R$^2$ are benzoyl groups which may optionally have, as a substituent, a halogen atom, lower alkyl group, lower alkoxyl group, nitro group, cyano group, hydroxyl group or amino group. Preferable are those which may optionally have, as a substituent, a halogen atom, lower alkyl group or lower alkoxyl group. More preferable is that which has, as a substituent, at least one lower alkoxyl group. The number of substituents is preferably 1 to 3. The substituent may be present at any of the ortho-, meta- and para-positions on the phenyl ring of the benzoyl group. Examples of benzyl groups which may optionally have at least one substituent represented by RI are benzyl groups which may optionally have on the phenyl ring, as a substituent, 1 to 3 of lower alkyl group, lower alkoxyl group, halogen atom or trifluoromethyl group. Preferable is unsubstituted benzyl group. Examples of halogen atoms are fluorine, chlorine, bromine and iodine atom, among which fluorine atom is preferable. Examples of useful lower alkyl groups are straight-chain or branched alkyl groups having 1 to 6 carbon atoms, such as methyl, ethyl, n-propyl, isopropyl, n-butyl, isobutyl, tert-butyl, pentyl, isopentyl and hexyl group. Preferable among these is methyl or ethyl group. Methyl group is more preferable. Examples of useful lower alkoxyl groups are straight-chain or branched alkoxyl groups having 1 to 6 carbon atoms, such as methoxy, ethoxy, n-propoxy, isopropoxy, n-butoxy, isobutoxy, sec-butoxy, tert-butoxy, pentyloxy, isopentyloxy and hexyloxy group, among which methoxy or ethoxy group is preferable. Methoxy group is more preferable.

Acyl groups represented by RI or RIA include widely an aliphatic acyl group and aromatic acyl group. Examples of aliphatic acyl groups are those having 2 to 6 carbon atoms, such as formyl, acetyl, propionyl, butyryl, isobutyryl, pentanoyl, hexanoyl, acryloyl, propioloyl, methacryloyl and crotonoyl. Examples of aromatic acyl groups are benzoyl, 3-toluyl, 4-toluyl, 2-methoxybenzoyl, 2,4-dimethoxybenzoyl, α-naphthylcarbonyl and β-naphthylcarbonyl. Preferable among these is acetyl or benzoyl group. Acetyl group is more preferable.

Lower alkyl group shown by Q includes the above lower alkyl groups, among which methyl and ethyl groups are preferable. Methyl group is more preferable.

Halogen atom shown by X includes the above halogen atoms, among which chlorine atom is preferable.

Among the compounds of the formula (1) or (4), preferable are those having a ring structure wherein m or n is 0 [provided m and n are not 0 (zero) simultaneously], and more preferable are those wherein l is 1, m is 0 and n is 2. In case of the compound (1) wherein R is —OR$^1$, preferable are those wherein R$^1$ is a hydrogen atom or acetyl group, R$^2$ is benzoyl or benzoyl having lower alkoxyl group, halogen atom or lower alkyl group, Q is a hydrogen atom, and wherein l is 1, m is 0 and n is 2. Especially preferable are those wherein R$^1$ is a hydrogen atom, R$^2$ is a benzoyl having methoxy group, Q is a hydrogen atom, and wherein l is 1, m is 0 and n is 2.

Among the compounds of the formula (1) wherein R is oxo group, preferable are those wherein R$^2$ is a benzoyl or benzoyl having lower alkoxyl group or lower alkyl group, Q is a hydrogen atom or lower alkyl group, and wherein l is 1, m is 0 and n is 2. Especially preferable are those wherein $R^2$ is benzoyl having methoxy or methyl group, Q is a hydrogen atom or methyl group, and wherein l is 1, m is 0 and n is 2.

Further, in case of the compound (4), preferable are those wherein $R^2$ is benzoyl or benzoyl having lower alkoxyl group, halogen atom or lower alkyl group, $R^3$ is benzyl group, Q is a hydrogen atom, and wherein l is 1, m is 0 and n is 2. Especially preferable are those wherein $R^2$ is a benzoyl having methoxy group, Q is a hydrogen atom, and wherein l is 1, m is 0 and n is 2.

Examples of the compound of the above formula (1) or (4) are 7-benzyloxy-2-(4-methoxybenzoyl)-2-azabicyclo[4.3.0]nonan-3-one, 7-benzyloxy-2-benzoyl-2-azabicyclo[4.3.0]nonan-3-one, 7-benzyloxy-2-(4-fluorobenzoyl)-2-azabicyclot[4.3.0]nonan-3-one, 7-benzyloxy-2-(p-toluoyl)-2-azabicyclo[4.3.0]nonan-3-one, 7-benzyloxy-2-(2,4-dimethoxybenzoyl)-2-azabicyclo[4.3.0]nonan-3-one, 7-benzyloxy-3-(4-methoxybenzoyl)-3-azabicyclo[4.3.0]nonan-2-one, 7-benzyloxy-3-benzoyl-3-azabicyclo[4.3.0]nonan-2-one, 7-benzyloxy-3-(4-fluorobenzoyl)-3-azabicyclo[4.3.0]nonan-2-one, 7-benzyloxy-3-(p-toluoyl)-3-azabicyclo[4.3.0]nonan-2-one, 7-benzyloxy-3-(2,4-dimethoxybenzoyl)-3-azabicyclo[4.3.0]nonan-2-one, 7-hydroxy-2-(4-methoxybenzoyl)-2-azabicyclo[4.3.0]nonan-3-one, 7-hydroxy-2-benzoyl-2-azabicyclo[4.3.0]nonan-3-one, 7-hydroxy-2-(4-fluorobenzoyl)-2-azabicyclo[4.3.0]nonan-3-one, 7-hydroxy-2-(p-toluoyl)-2-azabicyclo[4.3.0]nonan-3-one, 7-hydroxy-2-(2,4-dimethoxybenzoyl)-2-azabicyclo[4.3.0]nonan-3-one, 7-hydroxy-3-(4-methoxybenzoyl)-3-azabicyclo[4.3.0]nonan-2-one, 7-hydroxy-3-benzoyl-3-azabicyclo[4.3.0]nonan-2-one, 7-hydroxy-3-(4-fluorobenzoyl)-3-azabicyclo[4.3.0]nonan-2-one, 7-hydroxy-3-(p-toluoyl)-3-azabicyclo[4.3.0]nonan-2-one, 7-hydroxy-3-(2,4-dimethoxybenzoyl)-3-azabicyclo[4.3.0]nonan-2-one, 7-acetoxy-2-(4-methoxybenzoyl)-2-azabicyclo[4.3.0]nonan-3-one, 7-acetoxy-2-benzoyl-2-azabicyclo[4.3.0]nonan-3-one, 7-acetoxy-2-(4-fluorobenzoyl)-2-azabicyclo[4.3.0]nonan-3-one, 7-acetoxy-2-(p-toluoyl)-2-azabicyclo[4.3.0]nonan-3-one, 7-acetoxy-2-(2,4-dimethoxybenzoyl)-2-azabicyclo[4.3.0]nonan-3-one, 7-acetoxy-3-(4-methoxybenzoyl)-3-azabicyclo[4.3.0]nonan-2-one, 7-acetoxy-3-benzoyl-3-azabicyclo[4.3.0]nonan-2-one, 7-acetoxy-3-(4-fluorobenzoyl)-3-azabicyclo[4.3.0]nonan-2-one, 7-acetoxy-3-(p-toluoyl)-3-azabicyclo[4.3.0]nonan-2-one, 7-acetoxy-3-(2,4-dimethoxybenzoyl)-3-azabicyclo[4.3.0]nonan-2-one, 6-benzyloxy-2-(4-methoxybenzoyl)-2-azabicyclo[3.3.0]octan-3-one, 7-benzyloxy-3-benzoyl-3-azabicyclo[3.3.0]octan-2-one,-8-benzyloxy-3-(4-fluorobenzoyl)-3-azabicyclo[5.3.0]decan-2-one, 2-benzyloxy-7-(p-toluoyl)-7-azabicyclo[4.3.0]nonan-8-one, 7-benzyloxy-2-(2,4-dimethoxybenzoyl)-2-azabicyclo[4.4.0]decan-3-one, 2-benzyloxy-8-(4-methoxybenzoyl)-8-azabicyclo[4.3.0]nonan-7-one, 7-benzyloxy-3-benzoyl-3-azabicyclo[4.4.0]decan-4-one, 8-benzyloxy-3-(4-fluorobenzoyl)-3-azabicyclo[5.4.0]undecan-4-one, 9-benzyloxy-4-(p-toluoyl)-4-azabicyclo[5.4.0]undecan-3-one, 3-(4-methoxybenzoyl)-3-azabicyclo[5.4.0]undecan-4,8-dione, 2-(4-methoxybenzoyl)-2-azabicyclo[4.4.0]decan-3,7-dione, 2-(4-methybenzoyl)-2-azabicyclo[4.3.0]nonan-3,7-dione, 2-(3-ethylbenzoyl)-2-azabicyclo[4.3.0]nonan-3,7-dione, 2-(2-methoxybenzoyl)-2-azabicyclo[4.3.0]nonan-3,7-dione, 2-(3-methoxybenzoyl)-2-azabicyclo[4.3.0]nonan-3,7-dione, 2-(4-methoxybenzoyl)-2-azabicyclo[4.3.0]nonan-3,7-dione, 2-(2,4-dimethoxybenzoyl)-2-azabicyclo[4.3.0]nonan-3,7-dione, 2-(2,6-dimethoxybenzoyl)-2-azabicyclo[4.3.0]nonan-3,7-dione, 2-(3,4-dimethoxybenzoyl)-2-azabicyclo[4.3.0]nonan-3,7-dione, 2-(3,5-dimethoxybenzoyl)-2-azabicyclo[4.3.0]nonan-3,7-dione, 2-(3,4,5-trimethoxybenzoyl)-2-azabicyclo[4.3.0]nonan-3,7-dione, 6-methyl-2-(4-methoxybenzoyl)-2-azabicyclo[4.3.0]nonan-3,7-dione and 6-ethyl-2-(4-methoxybenzoyl)-2-azabicyclo[4.3.0]nonan-3,7-dione.

Preferable examples are 7-benzyloxy-2-(4-methoxybenzoyl)-2-azabicyclo[4.3.0]nonan-3-one, 7-benzyloxy-2-benzoyl-2-azabicyclo[4.3.0]nonan-3-one, 7-benzyloxy-2-(4-fluorobenzoyl)-2-azabicyclo[4.3.0]nonan-3-one, 7-benzyloxy-2-(p-toluoyl)-2-azabicyclo[4.3.0]nonan-3-one, 7-benzyloxy-2-(2,4-dimethoxybenzoyl)-2-azabicyclo[4.3.0]nonan-3-one, 7-benzyloxy-3-(4-methoxybenzoyl)-3-azabicyclo[4.3.0]nonan-2-one, 7-benzyloxy-3-(4-fluorobenzoyl)-3-azabicyclo[4.3.0]nonan-2-one, 7-benzyloxy-3-(p-toluoyl)-3-azabicyclo[4.3.0]nonan-2-one, 7-benzyloxy-3-(2,4-dimethoxybenzoyl)-3-azabicyclo[4.3.0]nonan-2-one, 7-hydroxy-2-(4-methoxybenzoyl)-2-azabicyclo[4.3.0]nonan-3-one, 7-hydroxy-2-benzoyl-2-azabicyclo[4.3.0]nonan-3-one, 7-hydroxy-2-(4-fluorobenzoyl)-2-azabicyclo[4.3.0]nonan-3-one, 7-hydroxy-2-(p-toluoyl)-2-azabicyclo[4.3.0]nonan-3-one, 7-hydroxy-2-(2,4-dimethoxybenzoyl)-2-azabicyclo[4.3.0]nonan-3-one, 7-hydroxy-3-(4-methoxybenzoyl)-3-azabicyclo[4.3.0]nonan-2-one, 7-hydroxy-3-(4-fluorobenzoyl)-3-azabicyclo[4.3.0]nonan-2-one, 7-hydroxy-3-(p-toluoyl)-3-azabicyclo[4.3.0]nonan-2-one, 7-acetoxy-2-(4-methoxybenzoyl)-2-azabicyclo[4.3.0]nonan-3-one, 2-(4-methoxybenzoyl)-2-azabicyclo[4.4.0]decan-3,7-dione, 2-(4-methylbenzoyl)-2-azabicyclo[4.3.0]nonan-3,7-dione, 2-(2-methoxybenzoyl)-2-azabicyclo[4.3.0]nonan-3,7-dione, 2-(3-methoxybenzoyl)-2-azabicyclo[4.3.0]nonan-3,7-dione, 2-(4-methoxybenzoyl)-2-azabicyclo[4.3.0]nonan-3,7-dione, 2-(2,4-dimethoxybenzoyl)-2-azabicyclo[4.3.0]nonan-3,7-dione, 2-(2,4-dimethoxybenzoyl)-2-azabicyclo[4.3.0]nonan-3,7-dione, 2-(3,5-dimethoxybenzoyl)-2-azabicyclo[4.3.0]nonan-3,7-dione, 2-(3,5-dimethoxybenzoyl)-2-azabicyclo[4.3.0]nonan-3,7-dione, 2-(3,4,5-trimethoxybenzoyl)-2-azabicyclo[4.3.0]nonan-3,7-dione and 6-methyl-2-(4-methoxybenzoyl)-2-azabicyclo[4.3.0]nonan-3,7-dione.

More preferable examples are 7-hydroxy-2-(4-methoxybenzoyl)-2-azabicyclo[4.3.0]nonan-3-one, 7-hydroxy-2-benzoyl-2-azabicyclo[4.3.0]nonan-3-one, 7-hydroxy-2-(4-fluorobenzoyl)-2-azabicyclo[4.3.0]nonan-3-one, 7-hydroxy-2-(p-toluoyl)-2-azabicyclo[4.3.0]nonan-3-one, 7-hydroxy-2-(2,4-dimethoxybenzoyl)-2-azabicyclo[4.3.0]nonan-3-one, 7-hydroxy-3-(4-methoxybenzoyl)-3-azabicyclo[4.3.0]nonan-2-one, 7-hydroxy-3-(4-fluorobenzoyl)-3-azabicyclo[4.3.0]nonan-2-one, 7-hydroxy-3-(p-toluoyl)-3-azabicyclo[4.3.0]nonan-2-one, 2-(4-methylbenzoyl)-2-azabicyclo[4.3.0]nonan-3,7-dione, 2-(3-methoxybenzoyl)-2-azabicyclo[4.3.0]nonan-3,7-dione, 2-(2,4-dimethoxybenzoyl)-2-azabicyclo[4.3.0]nonan-3,7-dione, 2-(3,4-dimethoxybenzoyl)-2-azabicyclo[4.3.0]nonan-3,7-dione, 2-(3,5-dimethoxybenzoyl)-2-azabicyclo[4.3.0]nonan-3,7-dione and 2-(3,4,5-trimethoxybenzoyl)-2-azabicyclo[4.3.0]nonan-3,7-dione.

The bicyclolactam compound of the present invention wherein R is —$OR^1$ can be prepared, for example, by the following reaction process

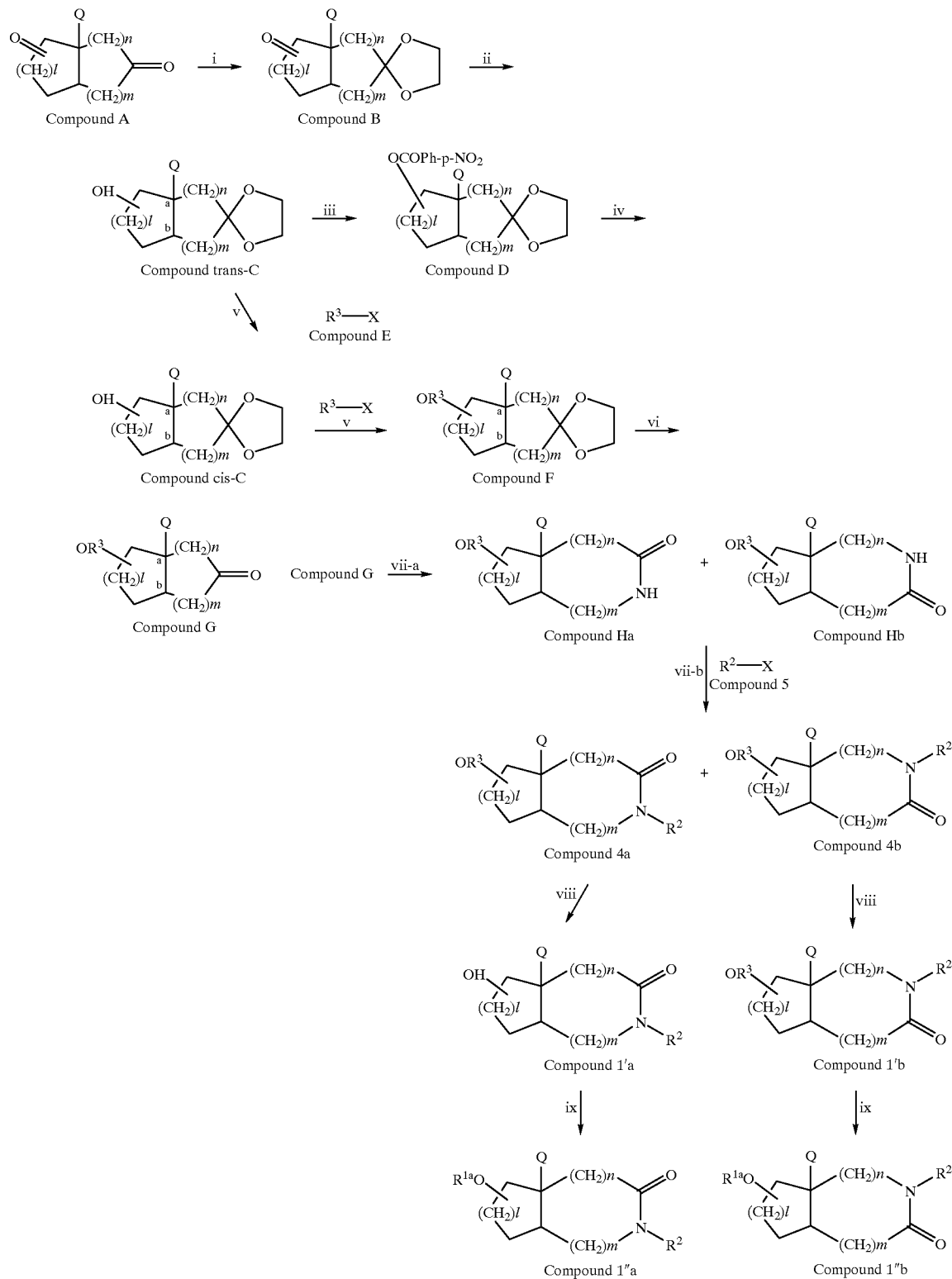

wherein Q, $R^2$, $R^3$, l, m and n are as defined above, $R^{1a}$ is acyl group, $R^4$ is a hydrogen atom, lower alkyl group, lower alkoxyl group, halogen atom or trifluoromethyl group, X is a halogen atom.

In the above, acyl group represented by $R^{1a}$ includes same acyl groups as above, lower alkyl group, lower alkoxyl group and halogen atom represented by $R^4$ includes same ones as above, and halogen atom shown by X includes same ones as above.

(Step i) A known compound A obtained by the method disclosed in J. Org. Chem., 42, 3764~3767 (1977), J. Chem. Soc., Chem. Commun., 24, 2759~60 (1994) or Chem. Lett., 9, 1437~40 (1985) is reacted with ethylene glycol in a suitable solvent in the presence of an acid catalyst to obtain a compound B. The solvent to be used is not particularly limited insofar as it does not participate in the reaction; it is, for example, an aromatic hydrocarbon such as benzene, toluene or xylene. Examples of useful acid catalysts are sulfuric acid, p-toluenesulfonic acid, methanesulfonic acid, trifluoromethanesulfonic acid and the like. The reaction is conducted using ethylene glycol and the acid catalyst each in an amount of About 1 to about 2 moles per mole of the compound A. The reaction temperature is 80° C. to a temperature around the boiling point of the solvent. For the completion of the reaction, the reaction time is 1 to 8 hours, preferable about 4 to about 7 hours. The compound B obtained by the invention can be used for the subsequent reaction, as isolated or without being isolated.

(Step ii) Next, the compound B is reacted with a reducing agent in a suitable solvent to obtain a compound trans-C which has a hydroxyl group in the trans-position to hydrogen atom attached to a bridgehead atom a. The solvent to be used is not limited specifically insofar as it does not participate in the reaction. Examples of such solvents are methanol, ethanol, propanol, isopropanol and like alcohols, dioxane, 1,2-dimethoxyethane, tetrahydrofuran and like ethers. Examples of useful reducing agents are lithium aluminum hydride, diisobutyl aluminum hydride, diborane, sodium boron hydride and the like. The reaction is conducted using the reducing agent in about 1 to about 1.5 moles per mole of the compound B. The reaction temperature is −5° C. to room temperature, preferably about 0 to about 10° C. The reaction time is preferably about 1 to about 3 hours. The compound trans-C resulting from the reaction can be used for the subsequent reaction (Step iii) or (Step v), as isolated or without being isolated.

(Step iii) The compound trans-C is reacted with p-nitrobenzoic acid, triphenylphosphine and diethyl azodicarboxylate in a suitable solvent to obtain a compound D. The solvent to be used is not limited specifically insofar as it does not participate in the reaction. Examples of such solvents are dioxane, 1,2-dimethoxyethane, tetrahydrofuran and like ethers, chloroform, dichloromethane, dichloroethane and like hydrocarbon halides. The reaction is conducted using the latter three reactants each in about 1 to about 3 moles per mole of the compound trans-C. The reaction temperature is −5 to 50° C., preferably about 0° C. to around room temperature. The reaction times is 1 to 15 hours, preferably about 6 to about 12 hours. The compound D resulting from the reaction can be used for the subsequent reaction, as isolated or without being isolated.

(Step iv) The compound D is hydrolyzed in a suitable solvent with use of an anion exchange resin to obtain a compound cis-C which has a hydroxyl group in the cis-position to hydrogen atom attached to a bridgehead atom a. The solvent to be used is not limited specifically insofar as it will not participate in the reaction. Examples of such solvents are methanol, ethanol, propanol, isopropanol and like alcohols. The reaction is conducted using the anion exchange resin in about 1 to about 10 moles per mole of the compound cis-D. The reaction temperature is room temperature to 100° C., and the reaction time is about 10 to about 24 hours. The compound cis-C resulting from the reaction can be used for the subsequent reaction, as isolated or without being isolated.

(Step v) The compound C obtained in (Step ii) or (Step iv) is reacted with a known compound E in a suitable solvent in the presence of a base to obtain a compopund F. The solvent to be used is not limited specifically insofar as it does not participate in the reaction. Examples of such solvents are N,N-dimethylformamide, N,N-dimethylacetamide, acetonitrile and like aprotic polar solvents, dioxane, 1,2-dimethoxyethane, tetrahydrofuran and like ethers. Examples of useful bases are trimethylamine, triethylamine, pyridine and like tertiary amines, potassium carbonate, sodium carbonate and like alkali metal carbonate, and potassium hydride, sodium hydride and like alkali metal hydrides. For the reaction, the base and compound E are used each in about 1 to about 2 moles per mole of the compound C. The reaction temperature is room temperature to 100° C., preferably room temperature to about 70° C. The reaction time is 8 to 30 hours, preferably about 20 to about 28 hours. The compound F resulting from the reaction can be used for the subsequent reaction, as isolated or without being isolated.

(Step vi) The compound F is subjected to a ketal removing reaction in a suitable solvent with use of an acid to obtain a compound G. The solvent is not limited specifically insofar as it does not participate in the reaction. Examples of solvents are alcohols such as methanol, ethanol, propanol and isopropanol, and ethers such as dioxane, 1,2-dimethoxyethane and tetrahydrofuran. Examples of useful acids are acetic acid, trifluoroacetic acid, oxalic acid and like organic acids, hydrochloric acid, hydrobromic acid, sulfuric acid, nitric acid and like inorganic acids. The reaction temperature is 0 to 60° C., preferably about 10 to about 70° C. The reaction time is about 2 to about 8 hours. The compound G resulting from the reaction can be used for the subsequent reaction, as isolated or without being isolated.

(Step vii-a) The compound G is reacted with hydroxylamine and sodium acetate in a suitable solvent to obtain an oxime of the compound G. The solvent is not limited specifically insofar as it does not participarte in the reaction. Examples of useful solvents are methanol, ethanol, propanol, isopropanol and like alcohols, dioxane, 1,2-dimethoxyethane, tetrahydrofuran and like ethers. Hydroxylamine and sodium acetate are used each in about 1.5 to 2 moles per mole of the compound G. The reaction temperature is 0 to 50° C., preferably room temperature. The reaction time is preferably 5 to 8 hours.

Subsequently, the resulting oxime of the compound G is reacted with p-toluenesulfonyl chloride in a suitable solvent in the presence of a base to obtain a p-tosylic acid ester of the compound G. Silica gel is added to the ester in the same solvent, followed by a Beckmann rearrangement reaction to obtain a mixture of compound Ha and compound Hb. The solvent to be used is not limited specifically insofar as it does not participate in the reaction. Examples of such, solvents are benzene, toluene, xylene and like aromatic hydrocarbons, chloroform, dichloromethane, dichloroethane and like hydrocarbon halides. Examples of useful bases are trimethylamine, triethylamine, pyridine and like tertiary amines. For the reaction, the base and p-toluenesulfonic chloride are used each in 2 to 3 moles per mole of the oxime of the compound G. The reaction temperature for tosylation is about 0 to 10° C., and the reaction time is about 4 to about 8 hours. The Beckmann rearrangement reaction in silica gel is conducted at a temperature of about 10 to about 30° C. for about 12 to about 24 hours.

(Step vii-b) The resulting mixture of compound Ha and compound Hb is reacted with a compound 5 in a suitable solvent in the presence of a base to obtain a compound 4a and compound 4b. The solvent is not limited specifically insofar as it does not participate in the reaction. Examples of useful solvents are benzene, toluene, xylene and like aromatic hydrocarbons, chloroform, dichloromethane, dichloroethane and like hydrocarbon halides. Examples of useful bases are tertiary amines such as trimethylamine, triethylamine and pyridine. For the reaction, compound 5 and the base are used each in about 1 to about 2 moles per mole of the mixture. The reaction temperature is about 0 to about 50° C., preferably about 10° C. to about 35° C. The reaction time is 12 to 36 hours, preferably about 24 to about 36 hours. The mixture of compound 4a or compound 4b resulting from the reaction can be isolated and purified by a usual method such as chromatography and the like. The compound 4a or compound 4b resulting from the reaction can be used for the subsequent reaction, as isolated or without being isolated.

(Step viii) The compound 4a or compound 4b is hydrogenated in a suitable solvent in the presence of a catalyst to obtain a compound 1'a or 1'b. The solvent is not limited specifically insofar as it does not participate in the reaction. Examples of useful solvents are methanol, ethanol, propanol, isopropanol and like alcohols, dioxane, 1,2-dimethoxyethane, tetrahydrofuran and like ethers, and methyl acetate, ethyl acetate and like acetic acid esters. As a catalyst is used for example palladium-charcoal and platinum. For the reaction, the catalyst is used preferably in the ratio of 0.5 to 1 by weight based on the compound 4a or 4b. The reaction temperature is preferably around room temperature to about 50° C. The reaction time is about 10 to about 20 hours.

(Step ix) The compound 1'a or compound 1'b is acylated in a suitable solvent by the method disclosed for example in JP-A-106,593/1986 to obtain a compound 1"a or 1"b. The solvent is not limited specifically insofar as it does not participate in the reaction. Examples of useful solvents are dichloromethane, dichloroethane, chloroform and like hydrocarbon halides, dioxane, tetrahydrofuran and like ethers, benzene, toluene and like aromatic hydrocarbons.

Usual acylation method is employed, and for example acid anhydride method and acid chloride method are applicable.

In acid anhydride method, the compound 1'a or compound 1'b is reacted with acid anhydride in a suitable solvent in the presence or absence of dimethylaminopyridine. As acid anhydride is used those having acyl group which should be introduced to $R^{1a}$. Examples thereof are acetic anhydride, propionic anhydride, butyric anhydride and benzoic anhydride. For the reaction, acid anhydride is used in about 1 to about 3 moles and dimethylaminopyridine is used in 0 to about 3 moles each per mole of the compound 1'a or compound 1'b. The reaction temperature is about 5 to about 50° C., preferably about 10° C. to around room temperature. The reaction time is 4 to 24 hours, preferably about 6 to about 12 hours.

In acid chloride method, the compound 1'a or compound 1'b is reacted with acyl halide ($R^{1a}X$) in a suitable solvent in the presence a dehydrohalogenation agent. Examples of dehydrohalogenation agents are sodium hydrogen carbonate, sodium carbonate, potassium carbonate, pyridine and triethylamine. The solvent includes those mentioned above. For the reaction, acyl halide is used in about 1 to about 3 moles per mole of the compound 1'a or compound 1'b. The reaction temperature is about −30 to about 100° C., preferably around room temperature to 80° C. The reaction time is 1 to 20 hours, preferably about 6 to about 12 hours.

Further, the bicyclolactam compound of the present invention wherein R is oxo group can be prepared, for example, by the following reaction process.

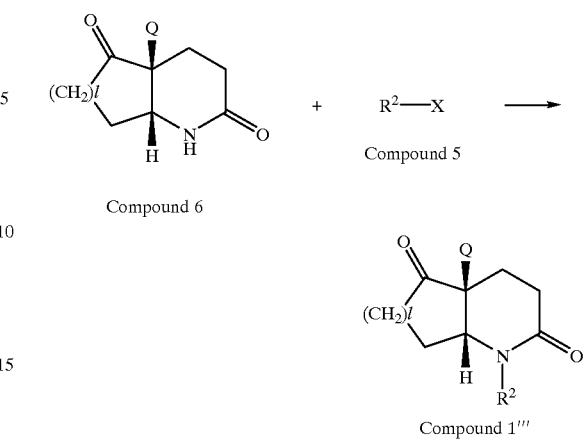

wherein Q, $R^2$, l and X are as defined above.

According too the above reaction step (vii-b), the compound 6 is reacted with the compound 5 in a suitable solvent in the presence of a base to obtain a compound 1'''. The solvent is not limited specifically insofar as it does not participate in the reaction. Examples of such solvents are benzene, toluene, xylene and like aromatic hydrocarbons, dichloromethane, dichloroethane and like hydrocarbon halides. Examples of useful bases are potassium carbonate, sodium carbonate and like inorganic bases, sodium methoxide, sodium ethoxide and like sodium alkoxides, trimethylamine, triethylamine, pyridine and like tertiary amines. For the reaction, the compound 5 and the base are used each in 1 to 2 moles per mole of the compound 6. The reaction temperature is about 0 to 50° C., preferably 10 to 35° C., and the reaction time is 1 to 24 hours, preferably about 6 to about 12 hours.

The compound 6 can be prepared by the following A, B or C process.

A process:

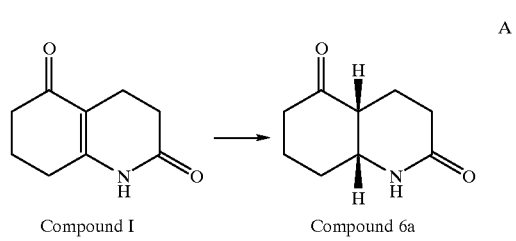

The compound I is obtained by cyclizing 2-cyanoethyl-1,3-cyclohexanedione according to the method disclosed in J. Org. Chem., 57, 2521 (1992). The compound I is reduced in a suitable solvent with hydrogen in the presence of palladium-charcoal to obtain the compound 6a wherein two hydrogen atoms on both of the bridgehead carbons have cis configuration. The solvent is not limited specifically insofar as it does not participate in the reaction. Examples of useful solvents are methanol, ethanol, isopropanol and like alcohols, dioxane, 1,2-dimethoxyethane, tetrahydrofuran and like ethers. For the reaction, palladium-charcoal is used in the ratio of 0.1 to 1.2 by weight based on the compound I. The hydrogen pressure is about 1 to 3 atom. The reaction temperature is 0 to 50° C., preferably 10° C. to around room temperature. The reaction time is preferably about 6 to about 12 hours. The resulting compound 6a can be used for the subsequent reaction for obtaining the present compound 1''', as isolated or without being isolated.

B process:

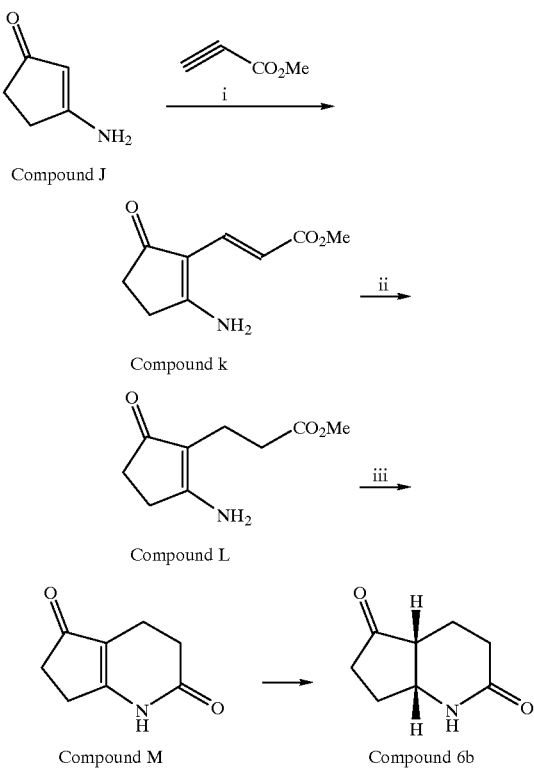

(Step B-i) A known compound J disclosed for example in Synthesis-, 176 (1991) is reacted in a suitable solvent with methyl ester of acetylenecarboxylic acid to obtain a compound K. The solvent is not limited specifically insofar as it does not participate in the reaction. Examples of useful solvents are N,N-dimethylformamide, N,N-dimethylacetamide, acetonitrile and like aprotic polar solvents, dioxane, 1,2-dimethoxyethane, tetrahydrofuran and like ethers. Methyl ester of acetylenecarboxylic acid is used in an excess amount, preferably about 4 to 7 moles per mole of the compound J. The reaction temperature is preferably about 120 to 150° C., and the reaction time is preferably about 6 to about 18 hours. The resulting compound K can be used for the subsequent reaction, as isolated or without being isolated.

(Step B-ii) The resulting compound K is reduced in a suitable solvent with hydrogen in the presence of palladium-charcoal to obtain the compound L. The solvent is not limited specifically insofar as it does not participate in the reaction. Examples of useful solvents are methanol, ethanol, isopropanol and like alcohols, dioxane, 1,2-dimethoxyethane, tetrahydrofuran and like ethers. For the reaction, palladium-charcoal is used in the ratio of 0.1 to 0.5 by weight based on the compound K. The hydrogen pressure is about 1 to 5 atom. The reaction temperature is 10 to 50° C., preferably 15 to 30° C. The reaction time is preferably about 2 to about 5 hours. The resulting compound L can be used for the subsequent reaction, as isolated or without being isolated.

(Step B-iii) The resulting compound L is heated without solvent to obtain a compound M. The heating is conducted at a temperature of about 170 to about 190° C. and for about 1 to about 3 hours.

Consequently, the compound M is reduced according to the method mentioned in the above A process to obtain a compound 6b. The resulting compound 6b can be used for the subsequent reaction for obtaining the present compound 1''', as isolated or without being isolated.

C process:

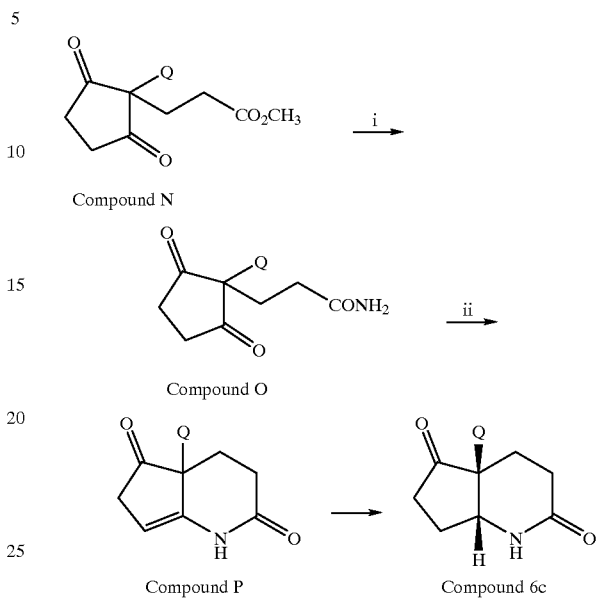

(Step C-i) To a known compound N discolsed for example in J. Org. Chem., 31, 1489 (1966) is added an excess amount of 25%-aqueous ammonia solution or methanol-ammonia for reaction, thereby a compound O is obtained. The reaction temperature is preferably about 15 to about 30° C. The reaction time is preferably about 3 to about 10 hours.

(Step C-in ) The resulting compound O is ring-colsed with dehydration according to the method disclosed for example in J. Org. Chem., 35, 3499 (1970) to obtain a compound P. The reaction temperature is about 70 to about 120° C., preferably around a boiling temperature of solvent. The reaction time is preferably about 2 to about 6 hours.

Consequently, the compound P is reduced according to the method mentioned in the above A process to obtain a compound 6c. The resulting compound 6c can be used for the subsequent reaction for obtaining the present compound 1''', as isolated or without being isolated.

The compound of the formula (1) thus obtained can be isolated and purified by a usual method such as recrystallization or column chromatography. The racemic compound obtained can be divided into the desired optical isomers, for example, by fractional recrystallization for the separation of salts from optically active acids or by passing a column packed with an optically active carrier. The stereoisomers can be individually separated off and purified by a usual method such as fractional crystallization or chromatography.

The present bicyclolactam compound is added to a pharmaceutical carrier to afford a pharmaceutical composition, particularly ah anxiolytic agent.

The anxiolytic agent having incorporated the present compound therein as an effective component can be given orally or parenterally—to mammals including man. The pharmaceutical preparations of the present invention are not limited specifically in the unit form of administration but can be in various forms in conformity with preventive or therapeutic purposes. These forms of preparations include, for example, oral preparations, injections, suppositories, external preparations (such as poultices and like plasters, ointments, creams and lotions), eye drops, nasal drops or sprays, etc.

The anxiolytic agent having incorporated the present compound therein as an effective component is prepared and used in the form of a composition having a desired conventional pharmaceutical carrier or excipient incorporated therein by a usual method.

Stated more specifically, examples of carriers for use in formulating the agent as tablets, encapsulated preparations, granules, powders, etc. for oral administration are excipients such as lactose, sucrose, sodium chloride, glucose, urea, starch, calcium carbonate, kaolin, crystalline cellulose and silicic acid, binders such as water, ethanol, propanol, syrup, glucose solution, starch solution, gelatin solution, carboxymethyl cellulose, hydroxypropyl cellulose, hydroxypropyl starch, shellac, methyl cellulose, ethyl cellulose, potassium phosphate and polyvinylpyrrolidone, disintegrators such as dried starch, sodium alginate, agar powder, laminaria powder, sodium hydrogencarbonate, calcium carbonate, polyoxyethylene sorbitan fatty acid esters, sodium laurylsulfate, stearic acid monoglyceride, starch and lactose, disintegration suppressants such as sucrose, stearic acid, cacao butter and hydrogenated oils, absorption promotors such as quaternary ammonium bases and sodium laurylsulfate, humectants such as glycerin and starch, absorbents such as starch, lactose, kaolin, bentonite and colloidal silicic acid, glazing agents such as purified talc, stearic acid salts, boric acid powder and polyethylene glycol, corrigents such as sucrose, bitter orange peel, citric acid and tartaric acid, etc. When required, the tablets can be those having a usual coating, such as sugar-coated tablets, gelatin-coated tablets, enteric-coated tablets, film-coated tablets, double-layer tablets and multi-layer tablets. The encapsulated preparation is made by mixing the present compound with carriers such as those exemplified above and filling the mixture into hard gelatin capsules or soft capsules.

Liquid preparations for oral administration include aqueous or oily suspensions, solutions, syrups and elixirs, and are prepared in the usual manner by adding a corrigent, buffer, stabilizer, flavoring agent., to the present compound.

In this case, examples of useful corrigents are those exemplified above, useful buffers include sodium citrate, and useful stabilizers include tragacanth, gum arabic and gelatin, etc.

Injections are aqueous or oily suspensions and solutions, or powdery fillers and freeze-dried preparations which are dissolved when to be used. Injections are prepared in the usual manner by adding to the present compound a pH adjusting agent, buffer, stabilizer, isotonic-agent, diluent, local anesthetic,. etc. Examples of pH adjusting agents and buffers for use in this case are sodium citrate, sodium acetate, sodium phosphate and the like. Examples of useful stabilizers are sodium pyrosulfite, EDTA, thioglycolic acid, thiolactic acid, etc. Examples of useful diluents are water, aqueous solution of lactic acid, ethyl alcohol, propylene glycol, ethoxylated isostearyl alcohol, polyoxyisostearyl alcohol, polyoxyethylene sorbitan fatty acid ester, etc. Examples of useful stabilizers are sodium pyrosulfite, EDTA, thioglycolic acid, thiolactic acid, etc. Examples of useful local anesthetics are procaine hydrochloride, lidocaine hydrochloride, etc.

In preparing suppositories, use can be made of carriers such as polyethylene glycol, lanolin, cacao fat, esters of higher alcohols, gelatin, semisynthetic glyceride, etc., and when required, surfactants such as Tween (trademark).

Ointments (pastes, creams, gels, etc.) are prepared by admixing with the present compound a base, stabilizer, lubricant, preservative, etc. which are usually used. Examples of bases are fluid paraffin, white petrolatam, bleached beeswax, octyldodecyl alcohol, paraffin and the like. Examples of useful preservatives are methyl p-hydroxybenzoate, ethyl p-hydroxybenzoate, propyl p-hydroxybenzoate and the like.

Plasters are prepared by applying the ointment, cream, gel, paste or the like to a usual support in the conventional manner. Examples of suitable supports are woven or nonwoven fabrics of cotton, staple fiber or chemical fiber, films of flexible polyvinyl chloride, polyethylene, polyurethane or the like, and foamed sheets of such material.

When required, the foregoing preparations may have further incorporated therein a coloring agent, preservative, perfume, flavoring, sweetener and the like, and other medicinals.

The method of administering the pharmaceutical preparation of the invention is not limited specifically but determined according to the form of preparation, age, sex and other conditions of the patient and degree of symptom of the patient. For example, tablets, pellets, powders, solutions, suspensions, emulsions, granules and capsules are given orally. Suppositories are introduced into the rectum. Injections are intravenously given singly or as mixed with a usual auxiliary solution such as glucose or amino acid solution. Further when required, they are singly administered intra-arterially, intramuscularly, intracutaneously, subcutaneously or intraperitoneally. Ointments are applied to the skin, mucous membrane of the oral cavity, etc. Plasters are applied to the skin.

The dosage of the effective component of the preparation of the invention can be suitably determined according to the mode of administration, age, sex and other conditions of the patient and degree of the symptom. Generally the effective component is administered at a daily dose usually of 0.001 to 50 mg/kg body weight, preferably 0.01 to mg/kg body weight. The present preparation can be given once or in about 2 to about four divided doses per day.

BEST MODE OF CARRYING OUT THE INVENTION

The present invention will be described below with reference to reference examples and examples. However, the invention is not limited by these examples.

REFERENCE EXAMPLE 1

Preparation of 6-oxo-bicyclo[3.3.0]octan-2-one=ethylene=acetal (Compound B-1)

A 9.62 g quantity of bicyclo[3.3.0]octan-2,6-dione which is known as disclosed for example in J. Org. Chem., 42, 3764~3767 (1977), 0.265 g of p-toluenesulfonic acid monohydrate and 4.54 g of ethylene glycol were dissolved in 50 ml of benzene, and the mixture was refluxed for reaction for 6 hours while removing water as an azeotropic mixture. After the reaction, the mixture was cooled to room temperature and allowed to stand for 15 minutes with addition of 3 g of sodium hydrogencarbonate. The resulting precipitate was filtered off and washed with benzene. The filtrate was concentrated to obtain a brown oily product, which was purified by column chromatography using 180 g of silica gel and hexane-ethyl acetate (5:1) to obtain 9.28 g of Compound mentioned above in the form of a colorless oily substance (yield: 73%)

$^1$H-NMR (CDCl$_3$) δ ppm: 1.80~2.45 (m, 10H), 3.95(s, 4H)

REFERENCE EXAMPLE 2

Preparation of (1RS, 2SR, 5RS)-2-hydroxybicyclo-[3.3.0]octan-6-one=ethylene=acetal (Compound trans-C-1)

A 9.23 g quantity of Compound obtained in Reference Example 1 was dissolved in 70 ml of methanol, and 1.93 g of sodium-boron hydride was added to the solution while cooling the solution in an ice-methanol bath. The mixuture was returned to room temperature 30 minutes later, followed by further reaction for 1 hour. The methanol was thereafter distilled off, 70 ml of water was added to the residue, and the mixture was subjected to extraction with 100 ml of dichloromethane and 50 ml of dichloromethane twice. The dichloromethane layer obtained was washed with 50 ml of saturated aqueous sodium chloride solution, then dried over anhydrous sodium sulfate and distilled for the removal of solvent, giving a colorless oily product. The product was purified by column chromatography using 150 g of silica gel and hexane-ethyl acetate (4:1 to 2:1) to obtain 6.63 g of Compound mentioned above in the form of a colorless oily substance (yield: 71%).

$^1$H-NMR (CDCl$_3$) δ ppm: 1.75~2.00(m, 8H), 2.10~2.80 (m, 2H) 3.90~4.18 (m, 1H), 3.94(s, 4H)

REFERENCE EXAMPLE 3

Preparation of (1RS, 2RS, 5RS)-2-(4-nitrobenzoyloxy)bicyclo-[3.3.0]octan-6-one=ethylene=acetal (Compound D-1)

A 3.68 g quantity of Compound obtained in Reference Example 2, 6.68 g of p-nitrobenzoic acid and 10.5 g of triphenylphosphine were dissolved in 70 ml of tetrahydrofuran, and a solution of 7.00 g of diethyl azodicarboxylate in 10 ml of tetrahydrofuran was added dropwise to the solution with ice cooling over a period of 10 minutes. The mixture was stirred with ice cooling for 1 hour, then returned to room temperature and further reacted for 16 hours. The solvent was distilled off from the reaction mixture, 50 ml of ether and 30 ml of hexane were added to the residue, and the resulting mixture was allowed to stand in a refrigerator for 1 day. The resulting precipitate (triphenylphosphine oxide) was filtered off and washed with hexane-ether (2:1). The filtrate obtained was concentrated to obtain a yellow oily product. The product was purified by column chromatography using 90 g of silica gel, hexane and hexane-ethyl acetate (10:1), giving 5.34 g of Compound mentioned above in the form of a light yellow oily substance (yield: 80%).

$^1$H-NMR (CDCl$_3$) δ ppm: 1.60~2.20(m, 8H), 2.45~2.90 (m, 2H), 3.94(s, 4H), 5.10~5.23(m, 1H), 8.24(s, 4H)

REFERENCE EXAMPLE 4

Preparation of (1RS, 2RS, 5RS)-2-hydroxybicyclo-[3.3.0]octan-6-one=ethylene=acetal (Compound cis-C-1)

A 12.85 g quantity of Compound obtained in Reference Example 3 was dissolved in 100 ml of methanol, 15 g of an anion exchange resin, Amberlite IR400 (OH$^-$) (product of Organo Co., Ltd.), was added to the solution, and the mixture was refluxed for 8 hours. Since the starting material still remained, 10 g of the anion exchange resin was further added to the mixture, followed by refluxing for 16 hours. The reaction mixture was returned to room temperature, filtered through High Flow Supercell (product of Nacalai Tesque Co., Ltd.) and washed with methanol. The resulting filtrate was concentrated and purified by column chromatography using 100 g of silica gel and hexane-ethyl acetate (3:1), whereby 6.52 g of Compound above-mentioned was obtained as a colorless oily substance (yiled: 92%).

$^1$-NMR (CDCl$_3$) δ ppm: 1.20~2.15(m, 8H), 2.30~2.80 (m, 2H) 3.80~4.10(m, 1H) 3.91(s, 4H)

REFERENCE EXAMPLE 5

Preparation of (1RS, 2RS, 5RS)-2-benzyloxybicyclo-[3.3.0]-octan-6-one=ethylene=acetal (Compound F-1)

A 6.40 g quantity of Compound obtained in Reference Example 4 was dissolved in 40 ml of N,N-dimethylformamide, 2.08 g of 60% sodium hydride was added to the solution, and the mixture was stirred at room temperature. The reaction temperature rose to about 45° C. with evolution of hydrogen. One hour later, the reaction mixture was cooled with ice, followed by addition of 6.3 ml of benzyl bromide. The mixture was returned to room temperature 30 minutes thereafter and stirred for 24 hours, followed by further reaction on a bath of 70° C. for 4 hours. The mixture was returned to room temperature, and 80 ml of ice water was added thereto. The resulting mixture was subjected to extraction with 60 ml of ether three times. The ethereal layer was washed with 20 ml of water three times and with 20 ml of saturated aqueous solution of sodium chloride and thereafter dried over anhydrous sodium sulfate. Removal of the solvent from the layer gave an oily product, which was then purified by column chromatography using 75 g of silica gel and hexane and hexane-ether (15:1), whereby 6.65 g of Compound mentioned above was obtained as an oily substance (yield: 70%).

$^1$H-NMR (CDCl$_3$) δ ppm: 1.60~2.10(m, 8H), 2.40~2.80 (m, 2H) 3.50~3.80(m, 1H), 3.90(s, 4H), 4.92(s, 2H), 7.31(s, 5H)

REFERENCE EXAMPLE 6

Preparation of (1RS, 2RS, 5RS)-2-benzyloxybicyclo-[3.3.0]-octan-6-one (Compound G-1)

A 1.94 g quantity of Compound obtained in Reference Example 5 was dissolved in 10 ml of tetrahydrofuran, and the solution was stirred for 6 hours with 3 ml of 2N hydrochloric acid added thereto. The tetrahydrofuran was distilled off from the resulting reaction mixture, followed by extraction with 20 ml of ether twice. The ethereal layer was washed with 10 ml of saturated aqueous solution of sodium hydrogencarbonate twice and then with 5 ml of saturated aqueous solution of sodium chloride, and dried over anhydrous sodium sulfate. Removal of the solvent from the layer give 1.60 g of Compound mentioned above as an oily substance (yield: 98%).

$^1$H-NMR (CDCl$_3$) δ ppm: 1.30~2.40(m, 8H), 2.60~3.00 (m, 2H), 3.70~3.90 (m, 1H),4.51 (s, 2H), 7.33 (s, 5H)

REFERENCE EXAMPLE 7

Preparation of cis-2-azabicyclo[4.4.0]decan-3,7-dione (Compound 6a)

Methanol (100 ml) was added to 1.5 g of 2,3,4,5,6,7,8-heptahydro-1(1H)-quinoline-2,5-dione which was known as disclosed for example in J. Org. Chem., 57, 2522 (1992). The mixture was subjected to reduction in the hydrogen stream (1 atm.) in the presence of 0.75 g of 10% palladium-carbon. The palladium-carbon was filtered oft and the solvent was removed. The residue was purified for isolation by column chromatography (silica gel, developer; chloroform:ethanol=10:1) to obtain 0.42 g of Compound mentioned above (yield: 28%). Table 1 shows analytical data.

REFERENCE EXAMPLE 8

Preparation of methyl 3-(3-amino-2-cyclopenten-1-one-2-yl)-acrylate (Compound K)

To 2 ml of dimethylacetamide were added 0.2 g of 3-amino-2-cyclopenten-1-one and 2 ml of methyl acetylenecarbonate. The mixture was heated with stirring at 120 to 125° C. for 19 hours. After cooled, 2 ml of ether was added and the precipitates were filtered and washed with ether to obtain 0.17 g of Compound mentioned above (yield: 46%).

m.p. 278~279° C. Elementary analysis; $C_9H_{11}NO_8$; Calcd. C, 59.67; H, 6.12; N, 7.73; Found C, 59.34; H, 6.47; N, 8.06.

REFERENCE EXAMPLE 9

Preparation of methyl 3-(3-amino-2-cyclopenten-1-one-2-yl)-propionate (Compound L)

To 200 ml of methanol were added 6.0 g of Compound K obtained in Reference Example 8 and 1.5 g of 10% palladium-charcoal. The mixture was reacted at room temperature in the hydrogen stream (2 atm.) for 3 hours. After reaction, the palladium-carbon was filtered off and the solvent was removed. The residue was crystallized from ether to obtain 5.9 g of Compound mentioned above (yield: 98%).

m.p. 223~224° C. Elementary analysis; $C_8H_{11}NO_3.0.2H_2O$ Calcd. C, 55.61; H, 6.65; N, 8.11; Found C, 55.58; H, 6.69; N, 8.31.

REFERENCE EXAMPLE 10

Preparation of 2,3,4,5,6,7-hexahydro-1(1H)-pyrindin-2,5-dione (Compound M)

A 2.8 g quantity of Compound L obtained in Reference Example 9 was heated with stirring without solvent at an oil bath temperature of 190 to 210° C. for one hour. After reaction, when hot, isopropanol was added. After cooling, the precipitates were filtered to obtain 1.7 g of Compound mentioned above (yield: 74%).

m.p. 247~248° C. Elementary analysis; $C_8H_9NO_2$ Calcd. C, 63.56; H, 6.00; N, 9.27; Found C, 63.25; H, 6.17; N, 9.30.

REFERENCE EXAMPLE 11

Preparation of cis-2-azabicyclo[4.3.0]nonan-3,7-dione (Compound 6b)

In 180 ml of methanol was suspended 3.8 g of Compound N obtained in Reference Example 10 and thereto was added 4 g of 10% palladium-charcoal. The mixture was reacted in the hydrogen stream (2 to 2.5 atm.) for 12 hours. After reaction, the palladium-charcoal was filtered off and the filtrate was concentrated. The residue was purified by column chromatography (silica gel, developer; ethyl acetate:methanol=10:1) to obtain 3.4 g of Compound mentioned above (yield: 89%). Table 1 shows analytical data.

REFERENCE EXAMPLE 12

Preparation of 2-methyl-2-(2-carbamoylethyl)-1,3-cyclopentanedione (Compound O-1)

A 1 ml quantity of 25% aqueous ammonia solution was added to 1.6 g of 2-methyl-2-(β-carbomethoxyethyl)-cyclopentan-1,3-dione which was known and disclosed for example in J. Org. Chem., 31, 1489 (1966). The mixture was reacted at room temperature for 5 hours. After reaction, 10 ml of tetrahydrofuran (THF) was added. The insolubles were filtered and recrystallized from ethanol to obtain 0.6 g of Compound mentioned above (yield: 41%).

m.p. 159~162° C.

REFERENCE EXAMPLE 13

Preparation of 2,3,4,4a,5,6-hexahydro-4a-methyl-1(1H)-pyrindin-2,5-dione (Compound P-1)

To 400 ml of toluene was added 4.42 g of Compound O-1 obtained in Reference Example 12, and thereto was added 0.6 g of tosyl acid. The mixture was heated with stirring for 3 hours with dehydration device attached. After reaction, the solvent was removed and the residue was recrystallized from ethanol-chloroform to obtain 3.0 g of Compound mentioned above (yield: 75%).

m.p. 228~230° C. Elementary analysis; $C_9H_{11}NO_2$ Calcd. C, 65.44; H, 6.71; N, 8.30; Found C, 65.13; H, 6.67; N, 8.30.

REFERENCE EXAMPLE 14

Preparation of cis-6-methyl-2-azabicyclo[4.3.0]-nonan-3,7-dione (Compound 6c-1)

Compound mentioned above was prepared in the same manner as in Reference Example 11 except that Compound P-1 obtained in Reference Example 13 was used in place of Compound M. Table 1 shows analytical data.

TABLE 1

(Compound 6)

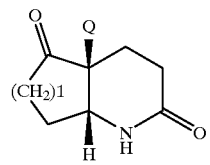

| Compd No. | Q | l | yield (%) | m.p. (° C.) | formula | elem. anal. calcd. (found) | | | MS (M+) |
|---|---|---|---|---|---|---|---|---|---|
| | | | | | | C | H | N | |
| 6a | H | 2 | 28 | 177~178 | $C_9H_{13}NO_2$ | 64.65 (64.65) | 7.84 (7.37) | 8.38 (8.34) | 167 |
| 6b | H | 1 | 71 | 140~142 | $C_8H_{11}NO_2.0.3H_2O$ | 60.59 (60.41) | 7.37 (7.08) | 8.83 (8.88) | 153 |
| 6c-1 | $CH_3$ | 1 | 77 | 129~131 | $C_9H_{13}NO_2$ | 64.65 (64.41) | 7.84 (7.58) | 8.38 (8.32) | 167 |

EXAMPLE 1

Preparation of (1RS, 6RS, 7RS)-7-benzyloxy-2-(4-methoxybenzoyl)-2-azabicyclo[4.3.0]nonan-3-one (Compound 4a-1) And (1RS, 6RS, 7RS)-7-benzyloxy-3-(4-methoxybenzoyl)-3-azabicyclo[4.3.0]nonan-2-one (Compound 4b-1)

A 1.54 g quantity of Compound obtained in Reference Example 6 was dissolved in 15 ml of tetrahydrofuran, followed by addition of 8 ml of water and thereafter by addition of 0.94 g of hydroxylamine hydrochloride and 1.84 g of sodium acetate trihydrate. Tetrahydrofuran was subsequently added to obtain a homogeneous mixture, which was then stirred at room temperature for 5 hours. The tetrahydrofuran was distilled off from the reaction mixture, followed by extraction with 80 ml of ethyl acetate. The ethyl acetate layer was washed with 10 ml of water, with 10 ml of saturated sodium hydrogencarbonate solution and subsequently with 10 ml of saturated aqueous solution of sodium chloride, and thereafter dried over anhydrous sodium sulfate. Distillation of the layer for the removal of the solvent gave 1.64 g of oxime of Compound of Reference Example 6 as a colorless oily substance.

A 1.60 g of the oxime obtained was dissolved in 16 ml of benzene, followed by addition of 3.11 g of p-toluenesulfonyl chloride and then by addition of 2.27 ml of triethylamine with ice cooling. The mixture was stirred for 4 hours with ice cooling and subsequently for 2 hours at room temperature, and thereafter diluted with 50 ml of ether. The resulting solution was washed with 10 ml of water, with 10 ml of 2N hydrochloric acid twice and subsequently with 10 ml of saturated aqueous solution of sodium chloride, and thereafter dried over anhydrous sodium sulfate. Removal of the solvent from the solution gave a yellow oily product. The product was dissolved in 50 ml of anhydrous benzene, followed by addition of 43 g of silica gel (Fuji Silysia, BW-300 as washed with 2N HCl and then thoroughly with water, and dried at 230° C. for 16 hours) and further by addition of anhydrous benzene in an amount of permitting stirring of the resulting mixture. The mixture was shaken on a water bath having a constant temperature of 25° C. for 18 hours. The reaction mixture was poured into a column packed with 20 g of silica gel, and 300 ml of benzene was passed through the column to cause an excess of p-toluenesulfonyl chloride to flow out. The solvent was thereafter changed for benzene-methanol (6:1) to obtain an eluate. The eluate still contained impurities and was therefore purified by column chromatography again using 30 g of silica gel, and chloroform and chloroform-methanol (50:1). The product was dried in a vacuum at room temperature to obtain 1.233 g of a light yellow oily substance. $^1$H-NMR analysis revealed that the product was a mixture of (1RS, 6RS, 7RS)-7-benzyloxy-2-azabicyclo[4.3.0]nonan-3-one and (1RS, 6RS, 7RS)-7-benzyloxy-3-azabicyclo[4.3.0]nonan-2-one approximately in the ratio of 2:1.

The mixture (1.18 g) obtained was dissolved in 15 ml of dichloromethane, 1.31 g of p-methoxybenzoyl chloride and 1.34 g of triethylamine were added to the solution, and the mixture was stirred at room temperature for 36 hours. With addition of 80 ml of ethyl acetate, the reaction:-mixture was washed with 20-ml of 2N hydrochlorid—acid twice, with 20 ml of saturated solution of sodium hydrogencarbonate twice and then with 10 ml of saturated aqueous solution of sodium chloride, and dried over anhydrous sodium sulfate. Removal of the solvent gave a brown oily product, which was then purified by column chromatography using 30 g of silica gel and hexane-ethyl acetate (4:1 to 3:1). The component eluted first was Compound 4b-1 mentioned above and obtained in an amount of 0.576 g as a yellow oily substance (yield: 25%). The component eluted thereafter was Compound 4a-1 mentioned above. The fraction was distilled for the removal of the solvent and recrystallized from ethanol, giving 1.05 g of the compound (yield: 46%). Tables 2 to 3 show analytical data.

EXAMPLE 2

Compounds 4a-2 to 4a-5 and Compounds 4b-2 to 4b-4 were prepared in the same manner as in Example 1 except that various benzoic chloride derivatives were used in place of p-methoxybenzoic chloride. Tables 2 to 3 show analytical data.

EXAMPLE 3

Preparation of (1RS, 6RS, 7RS)-7-hydroxy-2-(4-methoxybenzoyl)-2-azabicyclo-[4.3.0]nonan-3-one (Compound 1'a-1)

A 1.05 g quantity of (1RS, 6RS, 7RS)-7-benzyloxy-2-(4-methoxybenzoyl)-2-azabicyclo[4.3.0]nonan-3-one (Compound 4a-1) obtained in Example 1 was dissolved in 15 ml of dioxane, 0.50 g of 10% palladium-charcoal (product of Wako Junyaku Co., Ltd.) was added to the -solution, and the air in the reactor was removed by an aspirator and replaced by hydrogen repeatedly twice. The mixture was thereafter stirred in the hydrogen atmosphere (1 atm.) for 16 hours. The catalyst was filtered off and washed with dioxane. The resulting filtrate was concentrated to obtain a colorless oily product, which was then purified by column chromatography using 15 g of silica gel and chloroform. Removal of the solvent from the product afforded crystals, which were further recrystallized from ether, giving 0.64 g of Compound mentioned above in the form of a colorless powder (yield: 81%). Table 4 shows analytical data.

EXAMPLE 4

Compounds 1'a-2 to 1'a-5 were prepared in the same manner as in Example 3 except that Compounds 4a-2 to 4a-5 obtained in Example 2 were used as a starting material in place of Compound 4a-1. Similarly, Compounds 1'b-2 and 1'b-3 were prepared in the same manner as in Example 3 except that Compounds 4b-3 and 4b-4 obtained in Example 2 were used as a starting material in place of Compound 4b-1. Tables 4 to 5 show yield and analytical data.

EXAMPLE 5

Preparation of (1RS, 6RS, 7RS)-7-acetoxy-2-(4-methoxybenzoyl)-2-azabicyclo-[4.3.0]nonan-3-one (Compound 1"a-1)

A 0.29 g quantity of (1RS, 6RS, 7RS)-7-hydroxy-2-(4-methoxybenzoyl)-2-azabicyclo[4.3.0]nonan-3-one (Compound 1'a-1) obtained in Example 3 was dissolved in 10 ml of dichloromethane. With ice cooling, thereto were added 0.225 g of dimethylaminopyridine and then 0.2 g of acetic anhydride. The mixture was reacted at room temperature for 12 hours and then thereto was added 20 ml of dichloromethane. The reaction mixture was washed with 10 ml of 1N hydrochloric acid and then with 10 ml of saturated aqueous solution of sodium chloride, and dried over anhydrous sodium sulfate. Removal of the solvent gave a light brown oily product, which was then purified by column chromatography using 20 g of silica gel and chloroform-methanol (20:1) to obtain 0.23 g of Compound 1"a-1 as an oily substance (yield: 69%).

$^1$H-NMR(CDCl$_3$) δ ppm: 1.60~2.70(m, 9H), 2.08(s, 3H), 3.85(s, 3H), 4.70(q, 1H), 5.00~5.10(m, 1H), 6.88(d, 2H), 7.10(d, 2H)

TABLE 2

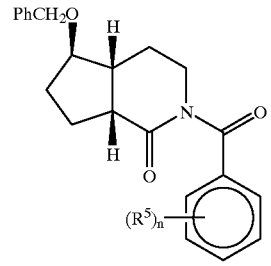

| Compd. No. | (R$^5$)n | yield (%) | m.p. (°C.) | $^1$H-NMR(CDCl$_3$) (δ ppm) |
|---|---|---|---|---|
| 4a-1 | 4-OCH$_3$ | 46 | 108.5~109.5 | 1.30~2.70(m, 10H), 3.70~4.00(m, 1H), 3.83(s, 3H), 4.54(s, 2H), 6.87(d, 2H), 7.34(s, 5H), 7.58(d, 2H) |
| 4a-2 | H | 26 | oil | 1.50~2.31(m, 6H), 2.40~2.57(m, 3H), 3.89(m, 1H), 4.52(m, 2H), 4.55(q, 1H), 7.26~7.58(m, 10H) |
| 4a-3 | 4-F | 27 | oil | 1.10~2.25(m, 6H), 2.25~2.75(m, 3H), 3.70~3.95(m, 1H), 4.55(dd, 2H), 4.70(q, 1H), 6.90~7.70(m, 9H) |
| 4a-4 | 4-CH$_3$ | 28 | 97~98 | 1.00~2.30(m, 6H), 2.36(s, 3H), 2.30~2.70(m, 3H), 3.70~4.00(m, 1H), 4.54(dd, 2H), 4.69(q, 1H), 7.10~7.60(m, 9H) |
| 4a-5 | 2,4-(OCH$_3$)$_2$ | 20 | oil | 1.42~2.06(m, 5H), 2.25~2.50(m, 4H), 3.73(s, 3H), 3.79(s, 3H), 3.86(m, 1H), 4.50(d, 1H), 4.53(d, 1H), 4.58(q, 1H), 6.50(d, 1H), 6.54(dd, 1H), 7.28(m, 1H), 7.32(d, 1H), 7.35(m, 4H) |

TABLE 3

| Compd No. | (R$^5$)n | yield (%) | m.p. (°C.) | $^1$H-NMR(CDCl$_3$) (δ ppm) |
|---|---|---|---|---|
| 4b-1 | 4-OCH$_3$ | 25 | oil | 1.30~3.30(m, 10H), 3.60~4.10(m, 1H), 3.83(s, 3H), 4.52(s, 2H), 6.86(d, 2H), 7.33(s, 5H), 7.54(d, 2H) |

TABLE 3-continued

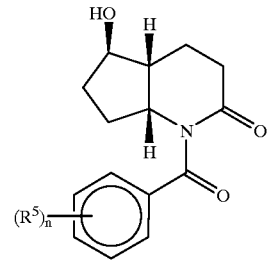

| Compd No. | (R$^5$)n | yield (%) | m.p. (°C.) | $^1$H-NMR(CDCl$_3$) (δ ppm) |
|---|---|---|---|---|
| 4b-2 | 4-F | 14 | 128~130 | 1.20~2.30(M, 6H), 2.40~2.80(m, 1H), 290~3.30(m, 1H), 3.40~3.65(m, 1H), 3.65~3.85(m, 1H), 3.95~4.25(m, 1H), 4.52(dd, 2H), 6.90~7.70(m, 9H) |
| 4b-3 | 4-CH$_3$ | 14 | oil | 1.20~2.30(m, 6H), 2.36(s, 3H), 2.40~2.80(m, 1H), 2.90~3.30(m, 1H), 3.40~3.65(m, 1H), 3.65~3.85(m, 1H), 3.95~4.25(m, 1H), 4.52(dd, 2H), 7.10~7.50(m, 9H) |
| 4b-4 | 2,4-(OCH$_3$)$_2$ | 17 | oil | 1.44~2.52(m, 7H), 3.02(m, 1H), 3.48(m, 1H), 3.69(s, 3H), 3.71(m, 1H), 3.79(s, 3H), 4.01(m, 1H), 4.48(d, 1H), 4.50(d, 1H), 6.49(d, 1H), 6.52(dd, 1H), 7.22(d, 1H), 7.28(m, 1H), 7.32~7.38(m, 4H) |

TABLE 4

| Compd No. | (R$^5$)n | yield (%) | m.p. (°C.) | $^1$H-NMR(CDCl$_3$) (δ ppm) |
|---|---|---|---|---|
| 1'a-1 | 4-OCH$_3$ | 81 | 120~121 | 1.20~2.70(m, 10H), 3.84(s, 3H), 3.90~4.30(m, 1H), 4.20(q, 1H), 6.88(d, 2H), 7.59(d, 2H) |
| 1'a-2 | H | 37 | 137.5~139 | 1.36~2.29(m, 7H), 2.45(t, 2H), 3.96(q, 1H), 4.56(q, 1H), 4.86(d, 1H), 7.41(m, 2H), 7.48~7.56(m, 3H) |
| 1'a-3 | 4-F | 39 | 110~112 | 1.20~2.80(m, 9H), 3.90~4.25(m, 1H), 4.73(q, 1H), 6.85~7.70(m, 4H) |
| 1'a-4 | 4-CH$_3$ | 27 | 131~133 | 1.20~2.70(m, 9H), 2.37(s, 3H), 4.00~4.25(m, 1H), 4.71(q, 1H), 7.10~7.60(m, 4H) |

TABLE 4-continued

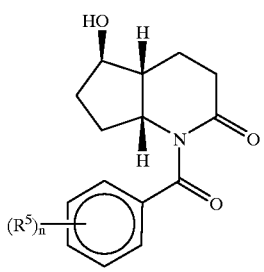

| Compd No. | $(R^5)n$ | yield (%) | m.p. (° C.) | $^1$H-NMR(CDCl$_3$) (δ ppm) |
|---|---|---|---|---|
| 1'a-5 | 2,4-(OCH$_3$)$_2$ | 56 | 114~115.5 | 1.28~2.27(m, 7H), 2.39(t, 3H), 3.73(s, 3H), 3.80(s, 3H), 3.93(m, 1H), 4.59(q, 1H), 4.84 (d, 1H), 6.49(d, 1H), 6.54 (dd, 1H), 7.31(d, 1H) |

TABLE 5

| Compd No. | $(R^5)n$ | yield (%) | m.p. (° C.) | $^1$H-NMR(CDCl$_3$) (δ ppm) |
|---|---|---|---|---|
| 1'b-1 | 4-OCH$_3$ | 72 | 108~109 | 1.50~1.70(m, 2H), 1.90~2.40(m, 7H), 3.00~3.15(m, 1H), 3.50~3.65 (m, 1H), 3.80(s, 3H), 3.90~4.10 (m, 1H), 6.90(d, 2H), 7.55(d, 2H) |
| 1'b-2 | 4-F | 30 | oil | 1.20~2.55(m, 7H), 2.95~3.30(m, 1H), 3.40~3.80(m, 2H), 3.90~4.30 (m, 2H), 6.90~7.70(m, 4H) |
| 1'b-3 | 4-CH$_3$ | 28 | 104~106 | 1.30~2.60(m, 7H), 2.37(s, 3H), 2.90~3.30(m, 1H), 3.30~3.80(m, 1H), 3.90~4.30(m, 2H), 7.10~7.65 (m, 4H) |

EXAMPLE 6

Preparation of cis-2-(p-toluoyl)-2-azabicyclo-[4.3.0]nonan-3,7-dione (Compound 1'''-2)

In 20 ml of dichloromethane were dissolved 0.3 g of Compound 6b obtained in Example 11 and 0.39 g of 4-methylbenzoyl chloride. Thereto was added dropwise 0.38 ml of triethylamine with ice cooling. The mixture was reacted at room temperature for 12 hours. The reaction mixture was washed with 0.1N hydrochloric acid, with 0.1N aqueous solution of NaOH and then with water, and dried over anhydrous sodium sulfate. After dried, the solvent was removed and the residue was recrystallized to obtain 0.35 g of Compound mentioned above (yield: 66%). Table 6 shows analytical data.

EXAMPLE 7

Compound 1'''-1, and Compounds 1'''-3 to 1'''-11 were prepared in the same manner as in Example 6. Table 6 shows analytical data. Analytical data of NMR of Compounds 1'''-3 and 1'''-4 were shown below.

Compound 1'''-3

$^1$H-NMR(CDCl$_3$) δ ppm 1.80~2.90(m, 9H), 3.75(sr 3H), 3.94~4.20(m, 1H), 6.70~7.04(m, 2H), 7.22~7.48(m, 2H)

Compound 1'''-4

$^1$H-NMR(CDCl$_3$) δ ppm 1.70~2.80(m, 9H), 3.80(s, 3H), 4.84~5.10(m, 1H), 6.90~7.35(m, 4H)

TABLE 6

(Compound 1''')

| Compound No. | Q | l | $(R^5)n$ | yield (%) | m.p. (° C.) |
|---|---|---|---|---|---|
| 1'''-1 | H | 2 | 4-OCH$_3$ | 83 | 169~171 |
| 1'''-2 | H | 1 | 4-CH$_3$ | 66 | 148~149 |
| 1'''-3 | H | 1 | 2-OCH$_3$ | 85 | oil |
| 1'''-4 | H | 1 | 3-OCH$_3$ | 89 | oil |
| 1'''-5 | H | 1 | 4-OCH$_3$ | 49 | 115~117 |
| 1'''-6 | H | 1 | 2,4-(OCH$_3$)$_2$ | 74 | 153~154 |
| 1'''-7 | H | 1 | 2,6-(OCH$_3$)$_2$ | 68 | 144~145 |
| 1'''-8 | H | 1 | 3,4-(OCH$_3$)$_2$ | 56 | 123~125 |
| 1'''-9 | H | 1 | 3,5-(OCH$_3$)$_2$ | 81 | 135~136 |
| 1'''-10 | H | 1 | 3,4,5-(OCH$_3$)$_3$ | 79 | 150~151 |
| 1'''-11 | CH$_3$ | 1 | 4-OCH$_3$ | 62 | 111~113 |

Preparation Example 1

Tablet

| Compound 1'a-1 | 30 mg |
|---|---|
| Microcrystalline cellulose | 50 mg |
| Hydroxypropyl cellulose | 20 mg |
| Lactose | 47 mg |
| Talc | 2 mg |
| Magnesium stearate | 1 mg |

By the usual method, the above ingredients in the proportions given were made into tablets each weighing 150 mg.

Preparation Example 2

Granule

| Compound 1'a-5 | 10 mg |
|---|---|
| Lactose | 400 mg |
| Corn starch | 370 mg |
| Hydroxypropylmethyl cellulose | 20 mg |

The above ingredients in the proportions given were made into a granular preparation by the usual method in an amount of 800 mg per wrapper.

Preparation Example 3

Capsule

| | |
|---|---|
| Compound 1'b-1 | 55 mg |
| Lactose | 50 mg |
| Corn starch | 50 mg |
| Microcrystalline cellulose | 94 mg |
| Magnesium stearate | 1 mg |

By the usual method, the above ingredients in the proportions given were made into a granular preparation in an amount of 250 mg in each capsule.

Preparation Example 4

Injection

| | |
|---|---|
| Compound 1'''-8 | 10 mg |
| Sodium chloride | 3.5 mg |

The above ingredients in the proportions given were made into an injection by the usual method.

Preparation Example 5

Syrup

| | |
|---|---|
| Compound 1'''-9 | 50 mg |
| Purified sucrose | 60 g |
| Ethyl para-hydroxybenzoate | 5 mg |
| Butyl para-hydroxybenzoate | 5 mg |
| Perfume | suitable amount |
| Coloring agent | suitable amount |
| Purified water | suitable amount |

The above ingredients in the proportions given were made into a syrup by the usual method.

Preparation Example 6

Suppositories

| | |
|---|---|
| Compound 1'''-10 | 50 mg |
| Witepsol W-35 | 1400 mg |

(Trademark, a mixture of mono-, di- and triglyceride of saturated fatty acids from lauric acid to stearic acid, Dynamite Nobel Co., Ltd.)

By the usual method-, the above ingredients in the proportions given were made into suppositories.

Test examples are shown below in which 2-azabicyclo[3.4.0]nonane-2-one disclosed in International Public Disclosure No. WO 91/11434 was used as a comparison compound.

TEST EXAMPLE 1

Anticonflict Test

1. Experimental animals

Wistar rats (males weighing 140 to 160 g) were used for experiment in groups of 11 to 14.

2. Test agents and administration method

Compound 1'a-1, 1'a-5, 1 'b-1, 1'''-8, 1'''-9, the above comparison compound, diazepam or buspirone was suspended in a 0.5% sodium carboxymethyl cellulose solution, and the suspension was orally given to the animal in a volume of 5 ml/kg one hour before the start of experiment.

3. Experimental method and result

With reference to a method described in "Process in Anxiolytics and Antidepressants," edited by Showa Ueki and Tatsuo Furukawa, Ishiyaku Shuppansha, 56~59 (1981), the agents were tested using experimental boxes having a grid floor and a metal drinking tube in the floor. No water was supplied to the rats for 48 hours before the experiment. Upon lapse of first 24 hours, each group of rats were placed into the experimental box, permitted access to water for 30 seconds and caused to recognize the metal drinking tube. Upon lapse of further 24 hours with access to water prevented, the rats were placed into the box again and permitted access to water on condition that an electric current was passed between the metal drinking tube and the grid to give an electroshock for every 20 times of water drinking behavior to measure the frequency of water drinking behavior for 3 minutes. Anxiolytic effect was evaluated as relieving rate of anxiety as calculated by the following equation.

Relieving rate of anxiety$=(C-B)/(A-B)\times 100$

A: Frequency of water drinking behavior of a control group without an electroshock and no anxiety (frequency under no punishment)

B: Frequency of water drinking behavior of a group with an electroshock and anxiety (under punishment) and having been administerd a solvent containing no test compound (frequency under solvent-control group)

C: Frequency of water drinking behavior of a group having been administered a test compound and relieved anxiety (frequency under test com pound-administered group)

TABLE 7

Anticonflict Test

| Test compound | Dose (mg/kg) | Relieving rate of anxiety (%) |
|---|---|---|
| Compound 1'a-1 | 0.01 | 93 |
| | 0.1 | 86 |
| | 1.0 | 76 |
| Compound 1'a-5 | 0.01 | 89 |
| Compound 1'b-1 | 0.01 | 80 |
| Compound 1'''-8 | 0.01 | 96 |
| Compound 1'''-9 | 0.01 | 96 |
| Comparison Compound | 0.01 | 43 |
| | 0.1 | 44 |
| | 1.0 | 46 |
| Diazepam | 1.0 | −3 |
| Buspirone | 1.0 | 2 |

From the above, the present compound decreased anxiety almost nearly 100% at low doses of 0.01 to 0.1 mg/kg. Contrary, the comparison compound decreased anxiety up to 50% at the same dose. Diazepam and buspirone were found almost ineffective even at a dose of 1.0 mg/kg. Accordingly, the present compound exhibits extremely excellent anxiolytic effect.

TEST EXAMPLE 2

Muscle Relaxant Effect (Traction Method)

1. Experimental animals and administration method

Compound 1'a-1, the comparison compound, diazepam or buspirone was suspended in a 0.5% sodium carboxymethyl cellulose solution, and the suspension was orally administered to 3- to 4-week-old male ddY mice (in groups of 5) in a volume of 10 ml/kg one hour before the start of experiment.

2. Experimental method and result

With reference to a method described in Japan. J. Pharmacol., 49. 337~349(1989), the foreleg of the mouse was hung on a horizontal wire, having a diameter of 1.2 mm and fixed at a level of 30 cm, three times consecutively. If the hind leg did not touch the wire within 10 seconds each time, the result was interpreted as positive. Thus, $ED_{50}$ was determined for evaluation. Consequently, Compound 1'a-1 and the comparison compound exhibited no muscle relaxant effects even when given at a dose of 300 mg/kg. Diazepam and buspirone were 2.2 mg/kg and 427.8 mg/kg, respectively, in $ED_{50}$.

TEST EXAMPLE 3

Sedative Effect (Spontaneous Locomotor Activity)

1. Experimental animals and administration method

Compound 1'a-1, the comparison compound, diazepam or buspirone was suspended in a 0.5% sodium carboxymethyl cellulose solution, and the suspension was orally administered to 3- to 4-week-old male ddY mice (in groups of 5) in a volume of 10 ml/kg one hour before the start of experiment.

2. Experimental method and result

The test was conducted with reference to a method described in "Evaluation of Medicinal Efficacies (1), Pharmacological Test Method (I), Basic Lectures on Development of Pharmaceuticals," 50~54(1971). More specifically, the group of mice were given the test drug and thereafter measured the amount of spontaneous locomotor activity for 10 minutes per mouse using Animex MK-110 (Muromachi Kikai Co., Ltd.). When the amount of activity was up to 50% of the control group, the result was interpreted as positive to determine $ED_{50}$ for evaluation. Consequently, Compound 1'a-1 and the comparison compound exhibited no sedative effect even at a dose of 300 mg/kg. Diazepam and buspirone were 1.7 mg/kg and 149.7 mg/kg, respectively, in the above value.

TEST EXAMPLE 4

Effect on Central Nervous System Depressant (Ethanol Enhancing Method)

1. Experimental method and administration method

Compound 1'a-1, the comparison compound, diazepam or buspirone was suspended in a 0.5% sodium carboxymethyl cellulose solution, and the suspension was orally administered to 3- to 4-week-old male ddY mice (in groups of 6) in a volume of 10 ml/kg one hour before the start of experiment.

2. Experimental method and result

The test was conducted with reference to a method described in Japan. J. Pharmacol., 49, 337~349(1989). More specifically, the group of mice were intraperitoneally given 25% ethanol at a dose of 20 ml/kg and checked for the time interval between loss and recovery of the righting reflex. When the time measurement was in excess of twice the measurement of the control group, the result was interpreted as positive to determine $ED_{50}$ for evaluation. Consequently, Compound 1'a-1 and the comparison compound produced no ethanol enhancing effect even at a dose of 300 mg/kg. Diazepam and buspirone were 0.48 mg/kg and 120.1 mg/kg, respectively, in the value.

TEST EXAMPLE 5

Anticonvulsant Effect (Pentylenetetrazol-induced Convulsion Method)

1. Experimental method and administration method

Compound 1'a-1, the comparison compound, diazepam or buspirone was suspended in a 0.5% sodium carboxymethyl cellulose solution, and the suspension was orally administered to 3- to 4-week-old male ddY mice (in groups of 6) in a volume of 10 ml/kg one hour before the start of experiment.

2. Experimental method and result

The test was conducted with reference to a method described in "Evaluation of Medicinal Efficacies (1), Pharmacological Test Method (I), Basic Lectures on Development of Pharmaceuticals," 167~172(1971). More specifically, pentylenetetrazol was subcutaneously administered to the mouse at a dose of 150 mg/kg, and when the mouse did not die due to onset of convulsion within 60 minutes, the result was interpreted as positive to determine $ED_{50}$ for evaluation. Consequently, Compound 1'a-1 and the comparison compound exhibited no anticonvulsant effect even at a dose of 300 mg/kg. Diazepam and buspirone were 0.35 mg/kg and at least 300 mg/kg, respectively, in the value.

TEST EXAMPLE 6

Acute Toxicity Test

Five-week-old male ddY mice were used in groups of 6. The mice were orally given the test compound as suspended in a 0.5% sodium carboxymethyl cellulose solution and thereafter observed for 3 days to measure the number of deaths at each of doses. Table 8 shows the result.

TABLE 8

Acute Toxicity Test

| Test compound | Dose (mg/kg) | Number of animal | Number of death |
|---|---|---|---|
| Compound 1'a-1 | 2000 | 6 | 0 |
| Compound 1'a-1 | 3060 | 6 | 2 |
| Comprn. compnd | 2000 | 6 | 1 |
| Comprn. compnd | 3000 | 6 | 5 |

From the above, although 5 mice died among 6 mice at a dose of 3000 mg/kg in the comparison compound, only two mice died among 6 mice in the present compound. Accordingly, the present compound is low in toxicity and high in safety compared with the comparison compound.

INDUSTRIAL APPLICABILITY

The bicyclolactam derivative represented by the formula (1) has an excellent anxiolytic effect, is reduced in side effects such as sedative and muscle relaxant effects and is low in toxicity. Accordingly, the agent comprising the present compound as an effective component is useful for treating or preventing chronic or acute anxiety disorders (or anxiety and fear neuroses), such as panic disorder accompanied or not accompanied by agoraphobia, social phobia or simple phobia, obsessive-compulsive disorder (neurosis), stress disorder resulting from injury and systemic anxiety disorder, and other anxiety disorders, and also for relieving healthy persons and the aged of anxiety.

Additionally, the present invention is useful for treating or preventing the anxiety attendant on withdrawal symptoms due to drug dependance and/or drug addiction. Thus, the present invention is useful for allaying withdrawal symptoms due to alcohol dependence nicotine dependence, cocaine dependence and benzodiazepine dependence and withdrawal symptoms due to other drug dependence.

We claim:

1. A bicyclolactam compound represented by the following formula (1)

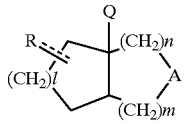
(1)

wherein

R is oxo or —OR$^1$, wherein R$^1$ is selected from the group consisting of a hydrogen atom, a C$_2$–C$_6$ acyl group, benzoyl, 3-toluyl, 4-toluyl, 2-methoxybenzoyl, 2,4-dimethoxybenzoyl, α-naphthylcarbonyl and β-naphthylcarbonyl;

A is a group (2) or (3)

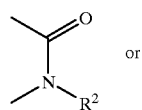
(2)

or

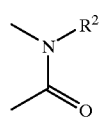
(3)

wherein R$^2$ is a benzoyl group which is unsubstituted or has 1–3 substituents each independently selected from the group consisting of a halogen atom, a C$_1$–C$_6$ alkyl group, a C$_1$–C$_6$ alkoxyl group, a nitro group, a cyano group, a hydroxyl group and an amino group;

Q is hydrogen or a straight-chained or branched C$_1$–C$_6$ alkyl group;

l is 1;

m is 0; and n is 2.

2. The bicyclolactam compound of claim 1, wherein R is —OR$^1$ wherein R$^1$ is a hydrogen atom or an acetyl group, R$^2$ is an unsubstituted benzoyl group or a benzoyl group substituted by a straight-chained or branched C$_1$–C$_6$ alkyloxy group and Q is a hydrogen atom.

3. The bicyclolactam compound of claim 1, wherein R is —OR$^1$ wherein R$^1$ is a hydrogen atom, R$^2$ is a benzoyl group substituted by a methoxy group and Q is a hydrogen atom.

4. The bicyclolactam compound of claim 1, herein R is oxo and R$^2$ is an unsubstituted benzoyl group or a benzoyl group substituted by a straight-chained or branched C$_1$–C$_6$ alkyloxy group or a straight-chained or branched C$_1$–C$_6$ alkyl group.

5. The bicyclolactam compound of claim 4, wherein R$^2$ is a benzoyl group substituted by a methoxy group or a methyl group and Q is a hydrogen atom or a methyl group.

6. A process for preparing a bicyclolactam compound represented by the following formula (1')

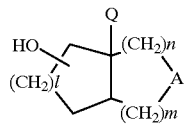
(1')

wherein

A is a group (2) or (3)

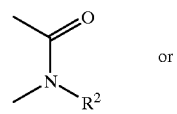
(2)

or

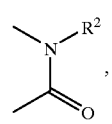
(3)

wherein R$^2$ is a substituted or unsubstituted benzoyl group;

Q is hydrogen or a straight-chained or branched C$_1$–C$_6$ alkyl group;

l is 1;

m is 0; and n is 2, the process comprising:

hydrogenating a compound of the formula (4)

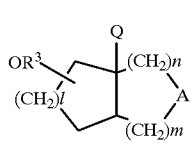
(4)

wherein A, Q, l, m, and n are as defined above, and

R$^3$ is an unsubstituted or substituted benzyl group, in a solvent in the presence of a catalyst, to produce the compound of the formula (1').

7. A bicyclolactam compound represented by the following formula (4)

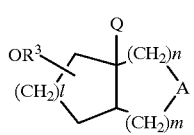
(4)

wherein

R$^3$ is a benzyl group which is unsubstituted or has 1–3 substituents each independently selected from the group consisting of a C$_1$–C$_6$ alkyl group, a C$_1$–C$_6$ alkoxyl group, a halogen atom and a trifluoromethyl group;

A is a group (2) or (3)

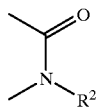
(2)

or

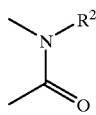
(3)

wherein $R^2$ is a benzoyl group which is unsubstituted or has 1–3 substituents each independently selected from the group consisting of a halogen atom, a $C_1$–$C_6$ alkyl group, a $C_1$–$C_6$ alkoxyl group, a nitro group, a cyano group, a hydroxyl group and an amino group;

Q is hydrogen or a straight-chained or branched $C_1$–$C_6$ alkyl group;

l is 1;

m is 0; and n is 2.

8. The bicyclolactam compound of claim 7, wherein $R^3$ is an unsubstituted benzyl group, $R^2$ is an unsubstituted benzoyl group or a benzoyl group having a substitutent selected from the group consisting of a straight-chained or branched $C_1$–$C_6$ alkyloxy group, a halogen atom and a straight-chained or branched $C_1$–$C_6$ alkyl group, and Q is a hydrogen atom.

9. The bicyclolactam compound of claim 8, wherein $R^2$ is a benzoyl group substituted by a methoxy group.

10. A pharmaceutical composition comprising an effective amount of the bicyclolactam compound of claim 1 and a pharmaceutically acceptable carrier.

11. A method of treating anxiety in a patient, comprising administering to the patient an anxiety treating effective amount of the bicyclolactam compound of claim 1.

* * * * *

UNITED STATES PATENT AND TRADEMARK OFFICE
CERTIFICATE OF CORRECTION

PATENT NO.    : 6,004,975
DATED         : December 21, 1999
INVENTOR(S)   : Yamamoto et al.

It is certified that error appears in the above-identified patent and that said Letters Patent is hereby corrected as shown below:

<u>Title page,</u>
Item [63], insert therefor, -- PCT/JP95/00575, March 28, 1995, PCT/JP96/01565, June 7, 1996 --

Signed and Sealed this

Sixteenth Day of July, 2002

*Attest:*

JAMES E. ROGAN
*Attesting Officer*     *Director of the United States Patent and Trademark Office*